United States Patent
Roth et al.

(10) Patent No.: US 8,119,656 B2
(45) Date of Patent: Feb. 21, 2012

(54) INHIBITORS OF THE INFLUENZA VIRUS NON-STRUCTURAL 1 PROTEIN

(75) Inventors: Michael Roth, Dallas, TX (US); Beatriz Fontoura, Dallas, TX (US); Shuguang Wei, Plano, TX (US); Neal Satterly, Garland, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 296 days.

(21) Appl. No.: 12/315,945

(22) Filed: Dec. 8, 2008

(65) Prior Publication Data

US 2009/0170840 A1    Jul. 2, 2009

Related U.S. Application Data

(60) Provisional application No. 61/005,876, filed on Dec. 7, 2007.

(51) Int. Cl.
*A61K 31/473* (2006.01)
(52) U.S. Cl. ........................................ 514/296
(58) Field of Classification Search .................. None
See application file for complete search history.

(56) References Cited

U.S. PATENT DOCUMENTS

| 5,124,149 | A | 6/1992 | Shapiro et al. | 424/93.6 |
| 5,874,444 | A | 2/1999 | West | 514/310 |
| 7,579,468 | B2 * | 8/2009 | Babinski et al. | 546/103 |
| 2006/0182751 | A1 | 8/2006 | Gazzard et al. | 424/178.1 |
| 2007/0134243 | A1 | 6/2007 | Gazzard et al. | 424/145.1 |

FOREIGN PATENT DOCUMENTS

| EP | 0 728 745 | 8/1996 |
| WO | WO 91/09850 | 7/1991 |
| WO | WO 97/27179 | 7/1997 |
| WO | WO 98/02449 | 1/1998 |
| WO | WO 98/07714 | 2/1998 |
| WO | WO 2006/027628 | 3/2006 |
| WO | WO 2006/060533 | 6/2006 |
| WO | WO 2007/023398 | 3/2007 |
| WO | WO 2007/146968 | 12/2007 |
| WO | WO 2008/050339 | 5/2008 |
| WO | WO 2008/116468 | 10/2008 |

OTHER PUBLICATIONS

Hampson et al., Medical Journal of Australia, 185(10), (Nov. 20, 2006), pp. S39-S43.*
Kim et al., Antivir. Chem. Chemotherapy, 10(4), (Jul. 1999), pp. 141-154.*
Bachi et al., "The C-terminal domain of TAP interacts with the nuclear pore complex and promotes export of specific CTE-bearing RNA substrates," *RNA*, 6:136-158, 2000.
Blevins et al., "Complex formation among the RNA export proteins Nup98, Rae1/Gle2, and TAP," *J. Biol. Chem.*, 278:20979-20988, 2003.
Boehmer et al., "Depletion of a single nucleoporin, Nup107, prevents the assembly of a subset of nucleoporins into the nuclear pore complex," *Proc. Natl. Acad. Sci. USA*, 100:981-985, 2003.
Brown et al., "A mutation in the Schizosaccharomyces pombe rae1 gene causes defects in poly(A)+ RNA export and in the cytoskeleton," *J. Biol. Chem.*, 270:7411-7419, 1995.
Enninga et al., Role of nucleoporin induction in releasing an mRNA nuclear export block, *Science*, 295:1523-1525, 2002.
Faria et al., "The nucleoporin Nup96 is required for proper expression of interferon-regulated proteins and functions," *Immunity*, 24:295-304, 2006.
Faria et al., "VSV disrupts the Rae1/mrnp41 mRNA nuclear export pathway," *Mol. Cell.*, 17:93-102, 2005.
Geiss et al., "Cellular transcriptional profiling in influenza A virus-infected lung epithelial cells: the role of the nonstructural NS1 protein in the evasion of the host innate defense and its potential contribution to pandemic influenza," *Proc. Natl. Acad. Sci. USA*, 99:10736-10741, 2002.
Her et al., "Inhibition of Ran guanosine triphosphatase-dependent nuclear transport by the matrix protein of vesicular stomatitis virus," *Science*, 276:1845-1848, 1997.
Jeganathan et al., "The Rae1-Nup98 complex prevents aneuploidy by inhibiting securin degradation," *Nature*, 438:1036-1039, 2005.
Kraemer and Blobel, "mRNA binding protein mrnp 41 localizes to both nucleus and cytoplasm," *Proc. Natl. Acad. Sci. USA.*, 94:9119-9124, 1997.
Palese and Shaw, In: *Orthomyxoviridae*: The Viruses and Their Replications, Fields Virology, 5th Ed., Chapter 47, 2007.
Pritchard et al., "RAE1 is a shuttling mRNA export factor that binds to a GLEBS-like NUP98 motif at the nuclear pore complex through multiple domains," *J. Cell. Biol.*, 145:237-254, 1999.
Satterly et al., "Influenza virus targets the mRNA export machinery and the nuclear pore complex," *Proc. Natl. Acad. Sci. USA*, 104:1853-1858, 2007.
Stutz and Izaurralde, "The interplay of nuclear mRNP assembly, mRNA surveillance and export," *Trends Cell. Biol.*, 13:319-327, 2003.
Vasu et al., "Novel vertebrate nucleoporins Nup133 and Nup160 play a role in mRNA export," *J. Cell. Biol.*, 155:339-354, 2001.

* cited by examiner

*Primary Examiner* — Phyllis G. Spivack
(74) *Attorney, Agent, or Firm* — Fulbright & Jaworski

(57) ABSTRACT

The present invention generally relates to compounds to treat viral infections and methods of their use. In particular, compounds of the present invention inhibit the activity of NS1 protein, thereby mitigating viral infection and, in particular, influenza virus infection. Accordingly, NS1 protein inhibitors and methods of treatment that employ such inhibitors are contemplated by the present invention.

9 Claims, 11 Drawing Sheets
(6 of 11 Drawing Sheet(s) Filed in Color)

FIG. 1
A
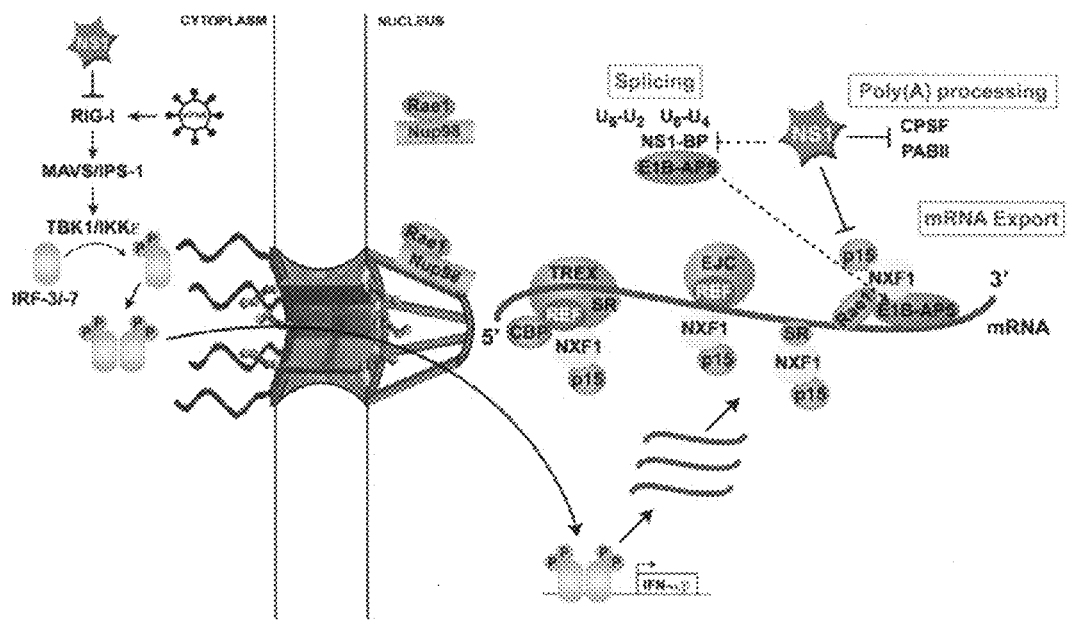
B
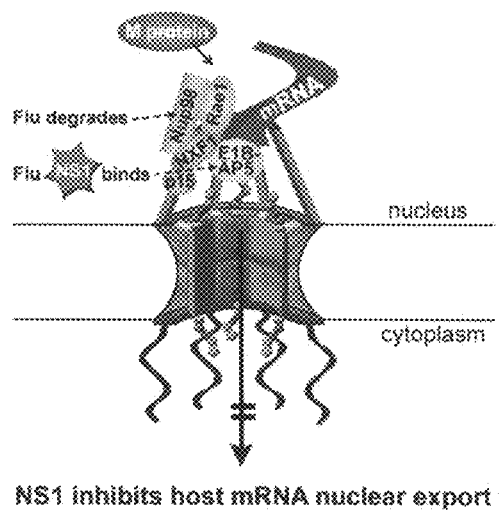
NS1 inhibits host mRNA nuclear export

FIG 3A-E

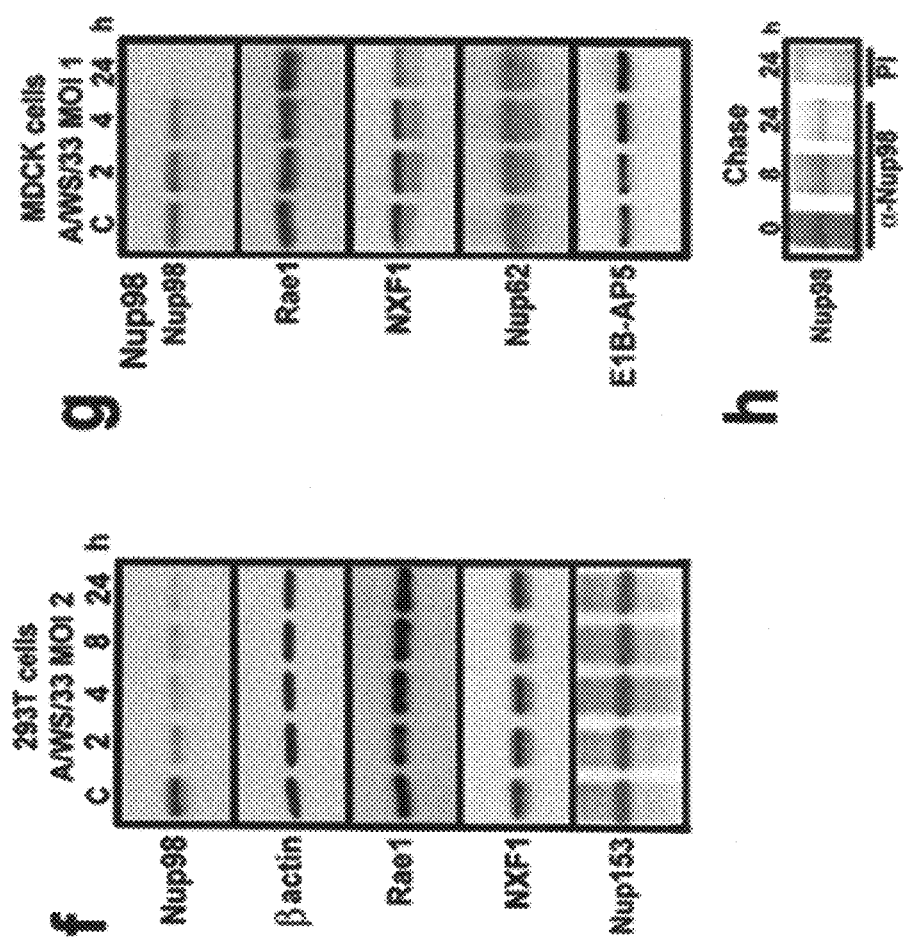
FIG. 3F-H

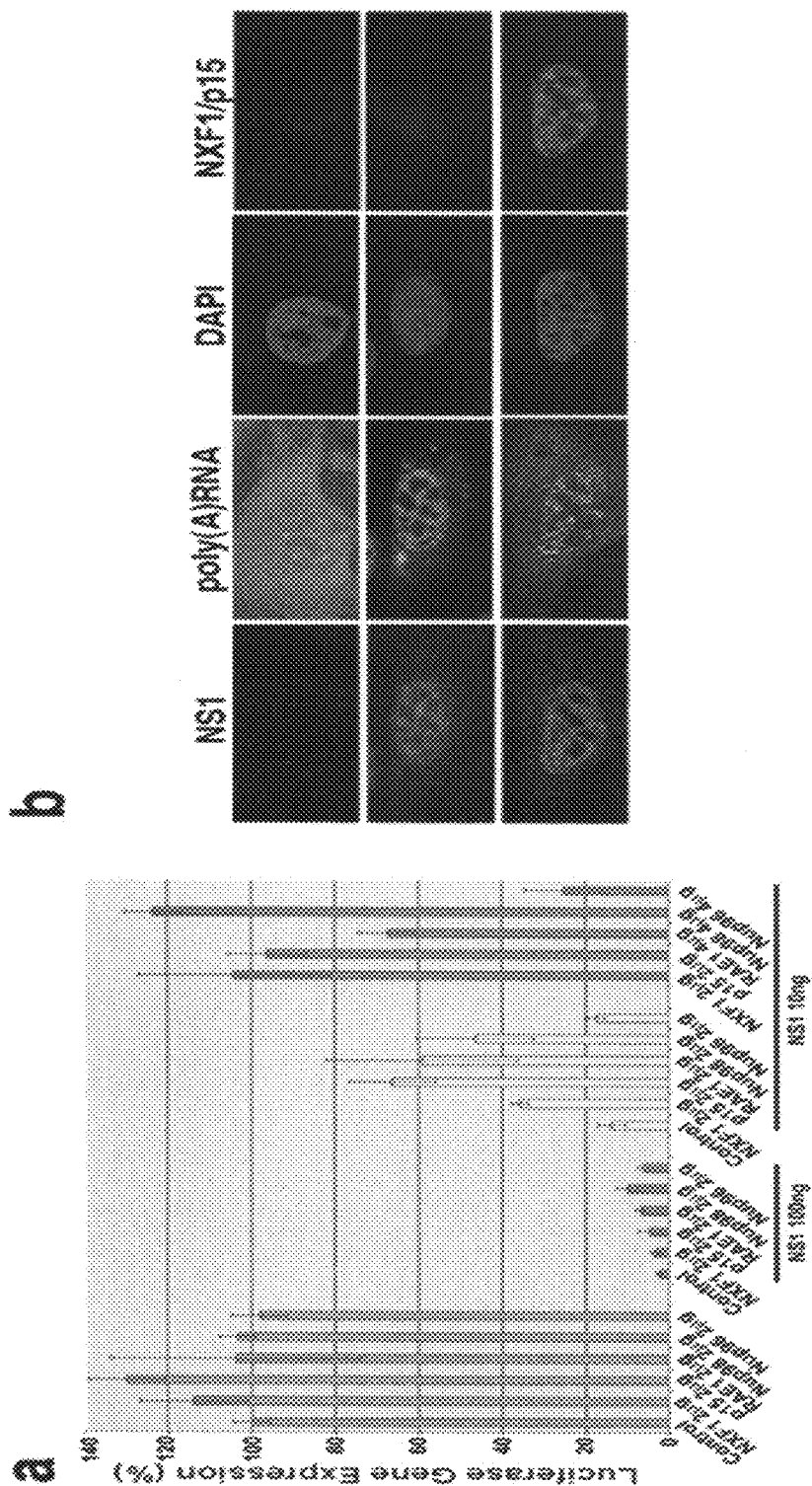
FIG. 4A-B

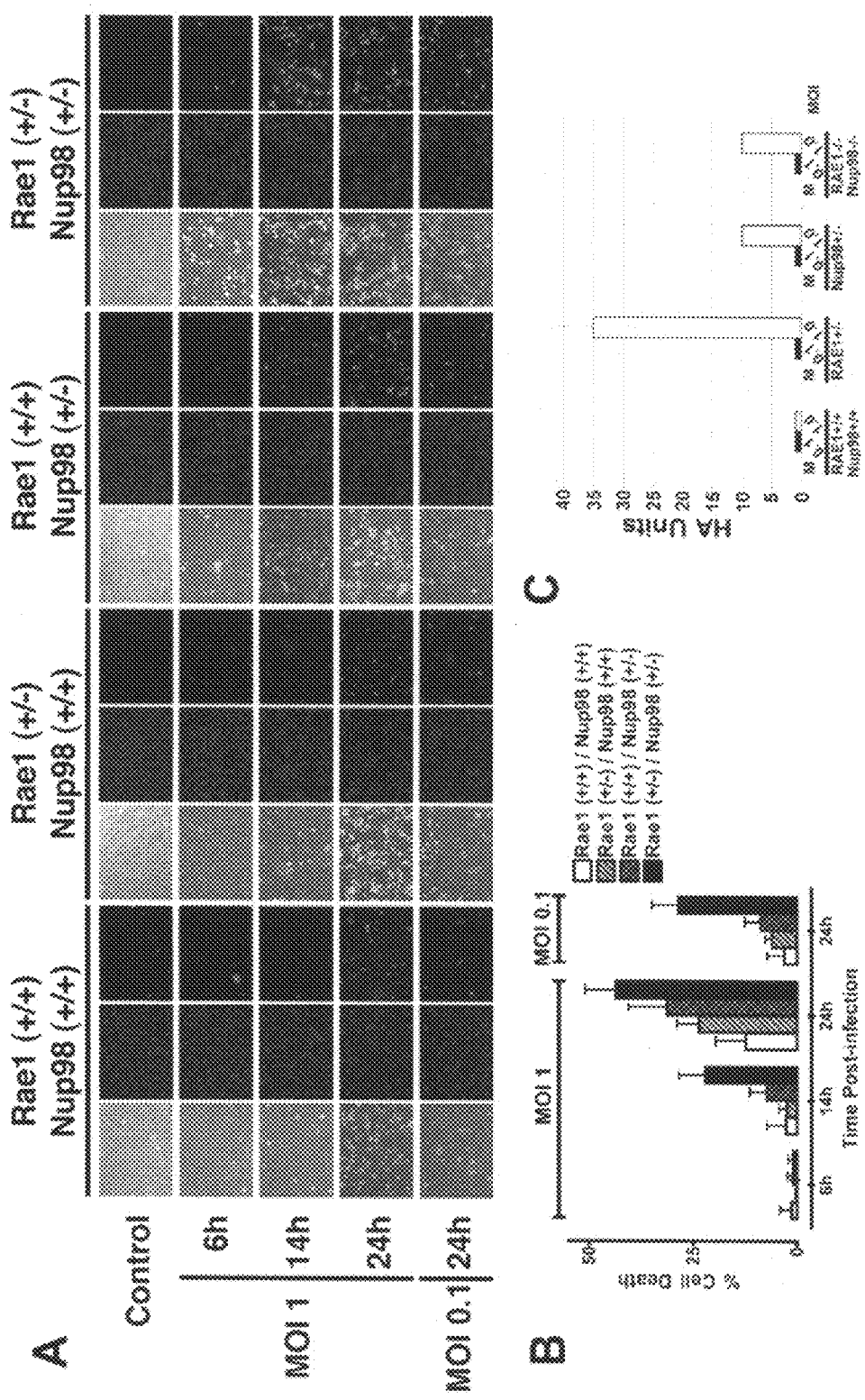
FIG. 5A-C

FIG. 7

| Compound structure | Inhibition of Virus Killing | Inhibition of NS1 (z score) | Analogs in Library | Compound structure | Inhibition of Virus Killing | Inhibition of NS1 (z score) | Analogs in Library |
|---|---|---|---|---|---|---|---|
| 1 | 40% | 3.8 | 21 | 5 | 31% | 4.0 | 3 |
| 2 | 38% | 3.6 | 58 | 6 | 30% | 3.8 | 8 |
| 3 | 36% | 5.2 | 5 | 7 | 26% | 6.2 | 46 |
| 4 | 33% | 4.1 | 33 | 8 | 50% | 3.6 | 14 |

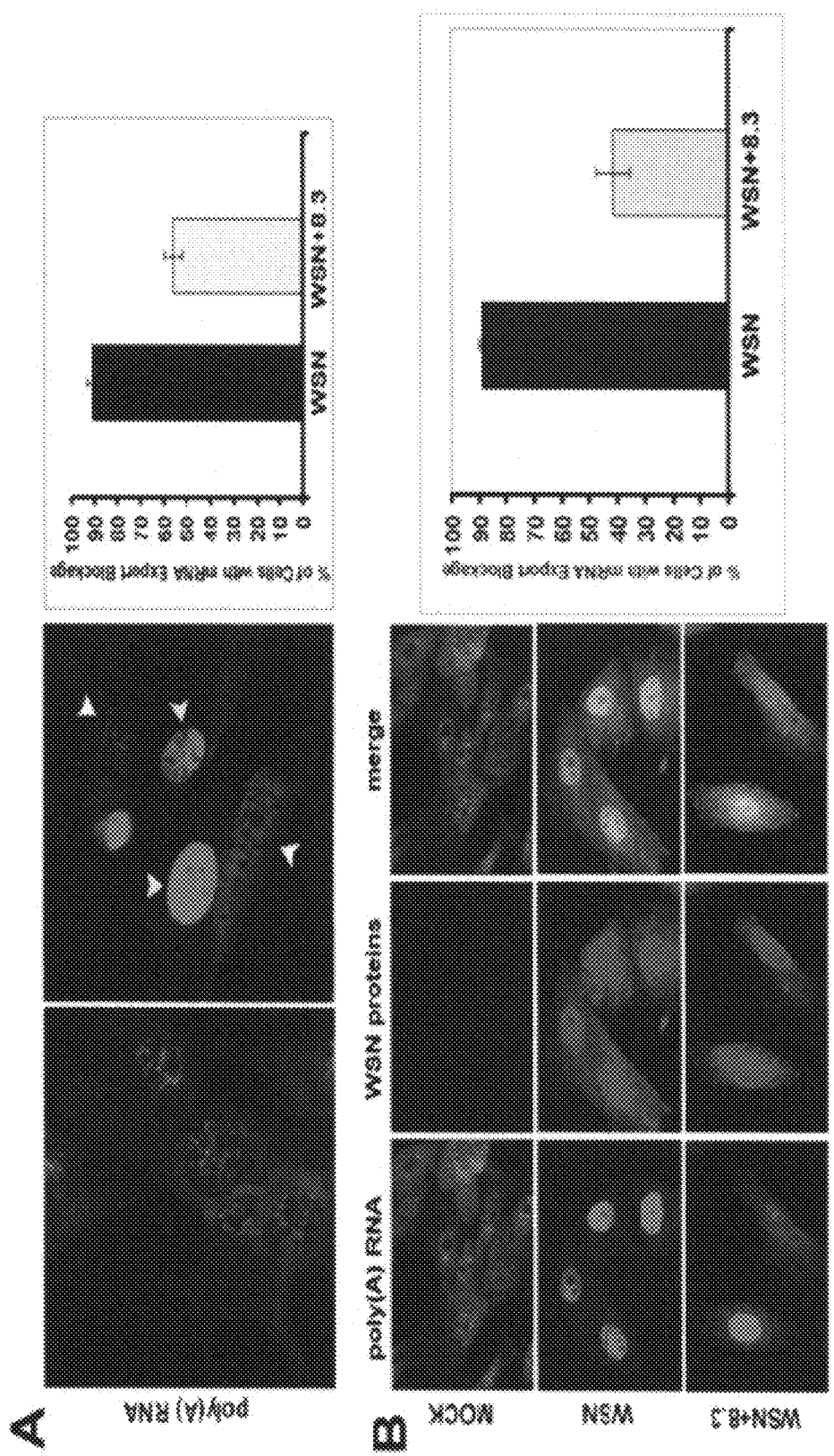
FIG 10A-B

INHIBITORS OF THE INFLUENZA VIRUS NON-STRUCTURAL 1 PROTEIN

This application claims priority to U.S. Provisional Patent Application No. 61/005,876 filed Dec. 7, 2007, which is incorporated herein by reference in its entirety.

This invention was made with government support under grant number NIH R01 GM067159-01 A1 awarded by the National Institutes of Health (NIH). The government has certain rights in the invention.

BACKGROUND OF THE INVENTION

1. Field of the Invention

The present invention generally relates to the fields of virology, molecular biology and medicine. More particularly, it concerns the discovery of compounds that inhibit influenza virus NS1 protein.

2. Description of Related Art

Influenza viruses cause approximately 36,000 deaths annually in the United States (91) and ~500,000 deaths worldwide per year (Smith et al., 2004). Strains that are extremely pathogenic have been responsible for high numbers of deaths worldwide, such as the 1918 pandemic which led to ~30 million deaths around the world (Webster, 1999). Currently, there are only two basic therapeutic approaches available for treating pandemic influenza: vaccination and inhibitors of virus infection or replication. Vaccination, although highly effective against certain strains, is limited by the highly mutable nature of the virus and must be reconstituted annually to address the changing viral ecology. A number of drugs have been developed that inhibit various steps in viral infection and replication, but they have demonstrated only limited efficacy. Thus, the availability of additional therapeutic modalities for the treatment of influenza viral diseases is presently unsatisfactory. Other treatments and routes of influenza virus mitigation are therefore needed.

SUMMARY OF THE INVENTION

The present invention generally provides compounds and their use as antiviral agents. More particularly, the inventors have identified small organopharmaceuticals that inhibit the activity of NS1 protein of influenza A virus, a major virulence factor. NS1 protein also inhibits interferon (IFN) gene induction and IFN-modulated immune responses. As such, the NS1 protein inhibitors described herein are also novel inhibitors of viral replication and pathogenesis that act by preventing NS1 protein-mediated inhibition of IFN-dependent immune responses to viral infection.

Accordingly, certain methods of the present invention contemplate a method of treating or preventing a viral infection in a patient comprising administering to said patient an effective amount of an NS1 protein inhibitor. Certain methods of the present invention are drawn to solely treatment of viral infections comprising administering to said patient an effective amount of an NS1 protein inhibitor. The patient may be a mammal, such as a mouse, rabbit, or human.

In certain embodiments of the present invention, NS1 protein inhibitors may be further defined as a compound of formula (I), (II), or (XII):

wherein: $X_1$ is O or S; $X_2$ is either not present or is hydrogen, O, $NO_2$, hydroxy, or COOH; $X_3$ is hydrogen, lower alkyl, O, S, 4-propoxyphenyl, thienyl, or $Y_1$ is —NH, —NCH$_3$, or S; $Y_2$ is C or N; $Y_3$ is —CH, —CH$_2$CH$_3$, —CH$_2$CH$_2$C$_6$H$_5$, —C-thienyl, —CC(O)NHC$_6$H$_4$I, —CC(O)NHCH$_2$furanyl, —N(CH$_2$)$_a$COOH, —NHCH(pyridinyl)(CH$_2$C(O)pyridinyl), —N—(CH$_2$)$_k$C$_6$H$_5$CO$_2$H, or O, wherein a is 1-5 and k is 0 or 1; $Y_4$ is C or N; $A_1$ is either not present or is —NH—, —CH$_2$—, or —CH—; $A_2$ is O, —NH—, —CO—, or —N—; $R_1$ is -continued

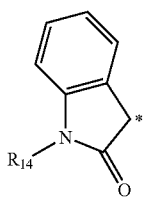

wherein $R_{13}$ is halogen; $R_{14}$ is lower alkyl, and wherein * indicates a point of attachment; $R_2$ is hydrogen, lower alkyl, phenyl, or

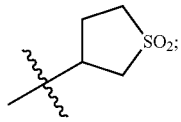

$R_3$ is hydrogen or —SO$_2$(CH$_2$)$_m$C(O)CH$_3$, wherein m is 1-4; $R_4$ is hydrogen, —C(O)CH$_3$, or —NO$_2$; $R_5$ is hydrogen, lower alkyl, or halogen; $R_6$ is hydrogen or hydroxy; $R_7$ is hydrogen, halogen, cyano, lower alkyl, or together with $R_8$ forms a phenyl group; $R_8$ is hydrogen, lower alkyl, —NO$_2$, lower alkoxy, cyano, —CH$_2$COOH, —SO$_2$(CH$_2$)$_m$C(O)CH$_3$, wherein m is 1-4, or together with $R_7$ forms a phenyl group; $R_9$ is hydrogen, halogen, or —NO$_2$; $R_{10}$ is hydrogen, —NO$_2$, N-piperidinyl, —C(O)NHCH$_2$furanyl,

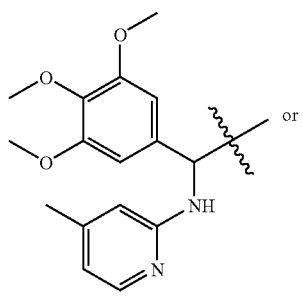

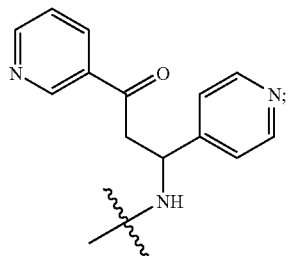

$R_{11}$ is hydrogen, hydroxy, or together with $R_{12}$ forms a phenyl group; $R_{12}$ is either not present or is hydrogen, lower alkyl, or together with $R_{11}$ forms a phenyl group; n is 0 or 1; and each bond numbered 1-5 is each independently a single or double bond; provided $R_4$-$R_8$ are not all hydrogen.

In particular embodiments, the compound of formula (XII) may be further defined as a compound of formula (III):

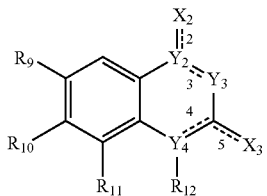

(III)

wherein: $X_2$ is either not present or is hydrogen, O, NO$_2$, hydroxy, or COOH; $X_3$ is hydrogen, lower alkyl, O, S, 4-propoxyphenyl, thienyl, or

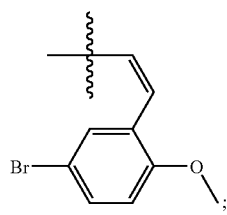

$Y_2$ is C or N; $Y_3$ is —CH, —C-thienyl, —CC(O)NHC$_6$H$_4$I, —CC(O)NHCH$_2$furanyl, —N(CH$_2$)$_a$COOH, —NHCH(pyridinyl)(CH$_2$C(O)pyridinyl), or O, wherein a is 1-4; $Y_4$ is C or N; $R_9$ is hydrogen or halogen; $R_{10}$ is hydrogen, —NO$_2$, —C(O)NHCH$_2$furanyl,

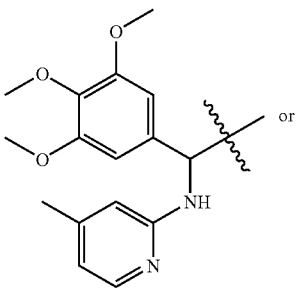

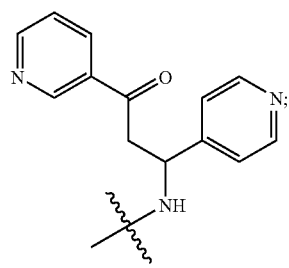

$R_{11}$ is hydrogen, hydroxy, or together with $R_{12}$ forms a phenyl group; $R_{12}$ is either not present or is hydrogen, lower alkyl, or together with $R_{11}$ forms a phenyl group; and each bond numbered 2-5 is each independently a single or double bond.

In other embodiments, the compound of formula (XII) is further defined as a compound of formula (XIII):

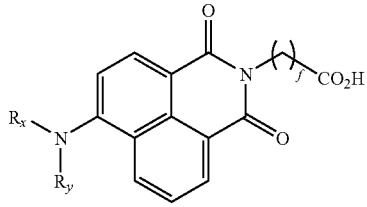
(XIII)

wherein: $R_x$ and $R_y$ are each independently lower alkyl, or $R_x$ and $R_y$ are joined to form a piperidinyl, pyrrolidinyl, or pyridinyl ring; and f is 1-5. In certain embodiments, $R_x$ and $R_y$ are joined to form a piperidinyl ring.

In certain embodiments, the NS1 protein inhibitor is further defined as a compound of formula (I), (II), or (III):

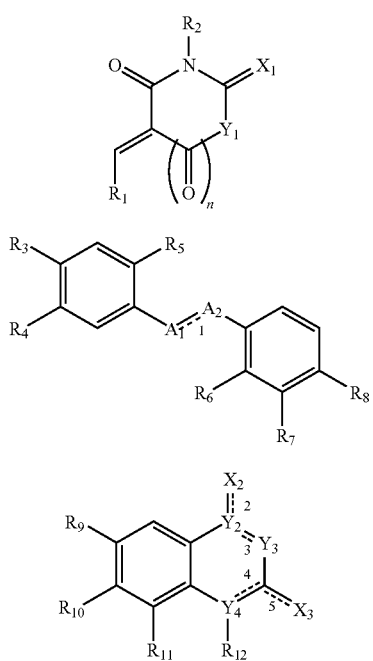
(I)

(II)

(III)

wherein: $X_1$ is O or S; $X_2$ is either not present or is hydrogen, O, —NO$_2$, hydroxy, or —COOH; $X_3$ is hydrogen, lower alkyl, O, S, 4-propoxyphenyl, thienyl, or

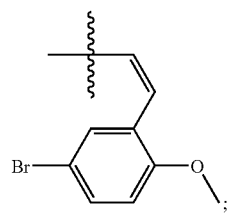

$Y_1$ is —NH, —NCH$_3$, or S; $Y_2$ is C or N; $Y_3$ is —CH, —C-thienyl, —CC(O)NHC$_6$H$_4$I, —CC(O)NHCH$_2$furanyl, —N(CH$_2$)$_a$COOH, —NHCH(pyridinyl)(CH$_2$C(O)pyridinyl), or O, wherein a is 1-4; $Y_4$ is C or N; $A_1$ is either not present or is —NH—, —CH$_2$—, or —CH—; $A_2$ is O, —NH—, —CO—, or —N—; $R_1$ is

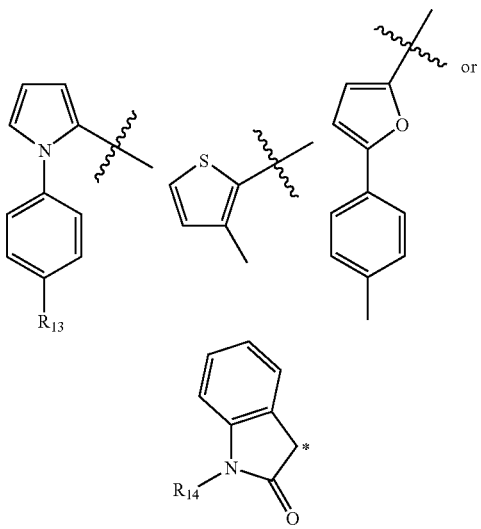

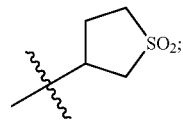

wherein $R_{13}$ is halogen; $R_{14}$ is lower alkyl, and wherein * indicates a point of attachment; $R_2$ is hydrogen, lower alkyl, phenyl, or $R_3$ is hydrogen or —SO$_2$(CH$_2$)$_m$C(O)CH$_3$, wherein m is 1-4; $R_4$ is hydrogen, —C(O)CH$_3$, or —NO$_2$; $R_5$ is hydrogen, lower alkyl, or halogen; $R_6$ is hydrogen or hydroxy; $R_7$ is hydrogen, halogen, cyano, lower alkyl, or together with $R_8$ forms a phenyl group; $R_8$ is hydrogen, lower alkyl, —NO$_2$, lower alkoxy, cyano, —CH$_2$COOH, —SO$_2$(CH$_2$)$_m$C(O)CH$_3$, wherein m is 1-4, or together with $R_7$ forms a phenyl group; $R_9$ is hydrogen or halogen; $R_{10}$ is hydrogen, —NO$_2$, —C(O)NHCH$_2$furanyl,

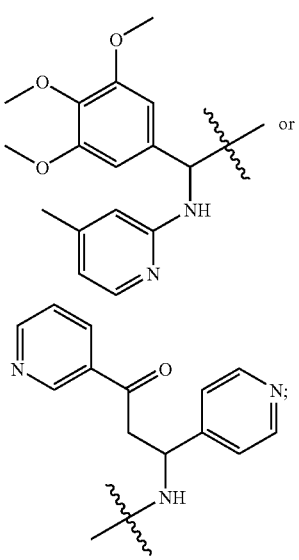

$R_{11}$ is hydrogen, hydroxy, or together with $R_{12}$ forms a phenyl group; $R_{12}$ is either not present or is hydrogen, lower alkyl, or together with $R_{11}$ forms a phenyl group; n is 0 or 1; and each bond numbered 1-5 is each independently a single or double bond; provided $R_4$-$R_8$ are not all hydrogen.

In certain embodiments of any generic that comprises a variable "a", a may be 1-5. In certain embodiments, a may be 1, 2, 3, 4 or 5, or any range derivable therein. In certain embodiments of any generic that comprises a variable "m", m may be 1-4. In certain embodiments, m may be 1, 2, 3 or 4, or any range derivable therein. In certain embodiments of any generic that comprises a variable "f", f may be 1-5. In certain embodiments, f may be 1, 2, 3, 4 or 5, or any range derivable therein.

In any method of the present invention that contemplates a viral infection, the viral infection may be influenza. The viral infection may be caused by, for example, influenza A virus. Other viruses are also contemplated. For example, the structure of NS1 protein of influenza B virus resembles NS1 protein of the influenza A virus: accordingly, influenza B virus may be associated with a viral infection of the present invention. Members of other virus families have been shown to be sensitive to interferon and to inhibit the production of interferon, and may do this through mechanisms similar to influenza A virus involving the same molecular pathways. Thus, compounds that inhibit the function of NS1 of influenza A virus may also block the inhibition of interferon by these other viruses. In this regard, therefore, certain embodiments of the present invention contemplate a viral infection caused by, e.g., a bunyavirus (such as LaCross virus), an arenavirus, or an encephalitis virus (e.g., West Nile virus). Other viruses contemplated by the present invention include rabies or a filovirus (e.g., Ebola virus and Marburg virus).

In certain embodiments, a compound of formula (I), (II), or (XII) may be further defined as a compound of formula (IV), (V), (VI), (VII), (VIII), (IX), (X), or (XI):

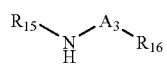
(IV)

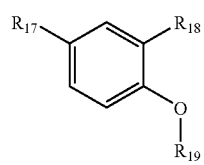
(V)

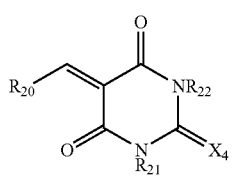
(VI)

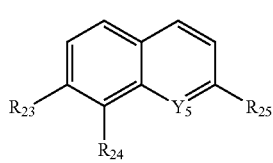
(VII)

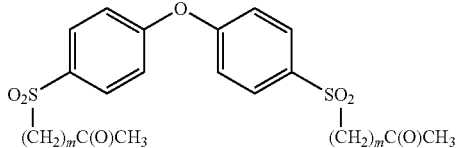
(VIII)

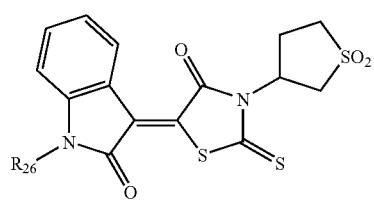
(IX)

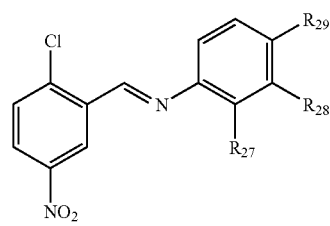
(X)

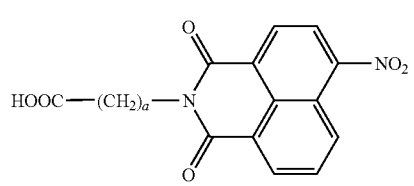
(XI)

wherein: $A_3$ is —C(O)— or —CH$_2$—; $X_4$ is O or S; $Y_5$ is N or C; $R_{15}$ is acetylphenyl, furanylmethyl, iodophenyl, or

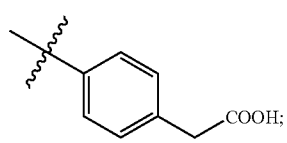

$R_{16}$ is halogen, toluoylmethyl,

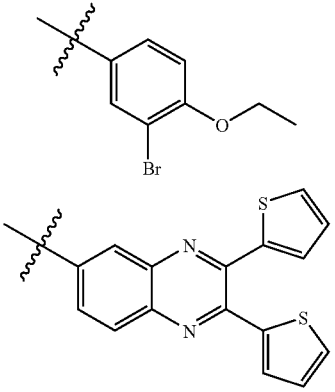

-continued

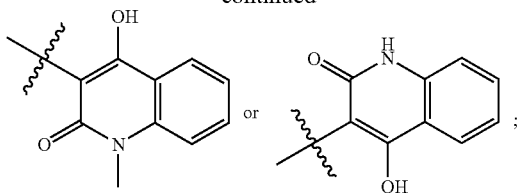

$R_{17}$ is halogen or

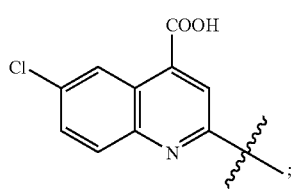

$R_{18}$ is hydrogen or

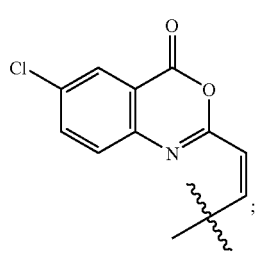

$R_{19}$ is lower alkyl; $R_{20}$ is methylthieno,

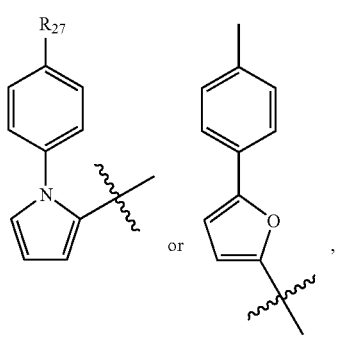

wherein $R_{27}$ is halogen; $R_{21}$ and $R_{22}$ are each independently hydrogen, lower alkyl, or phenyl; $R_{23}$ is

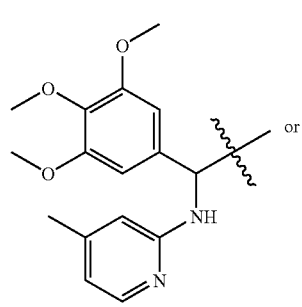

-continued

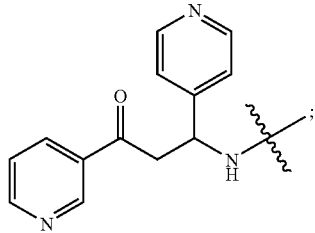

$R_{24}$ is hydrogen or hydroxy; $R_{25}$ hydrogen or lower alkyl; $R_{26}$ is lower alkyl; $R_{27}$ is hydrogen or hydroxy; $R_{28}$ is hydrogen, lower alkyl, cyano, or together with $R_{29}$ forms a phenyl group; $R_{29}$ is hydrogen, lower alkyl, cyano, lower alkoxy, —$NO_2$, or together with $R_{28}$ forms a phenyl group; $a=1-4$; and $m=1-4$.

In particular embodiments, a compound of formula (I), (II), or (XII) may be further defined as any one of the following:

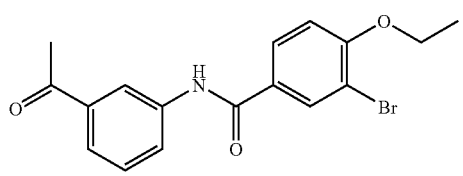

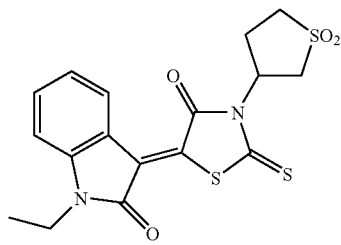

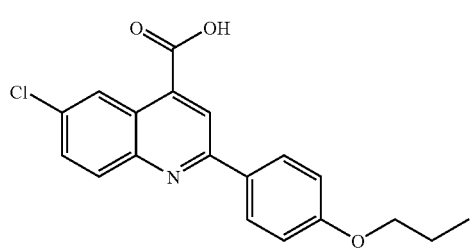

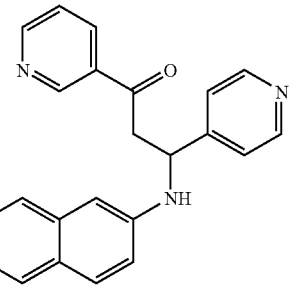

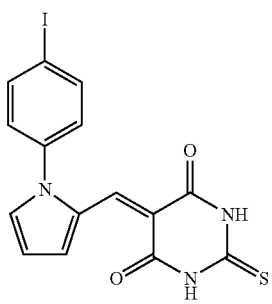
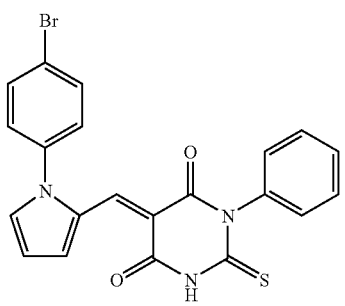
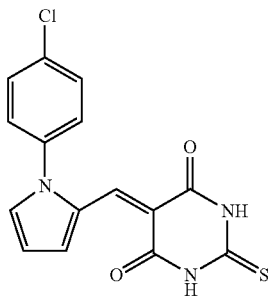
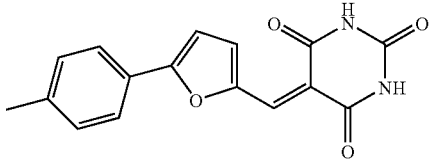
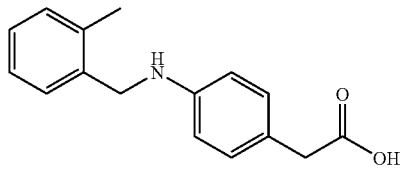
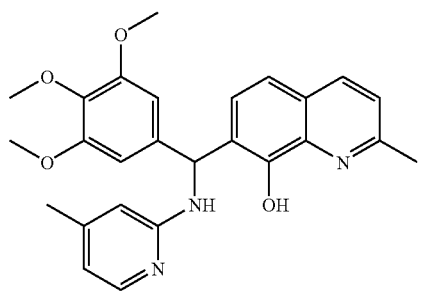
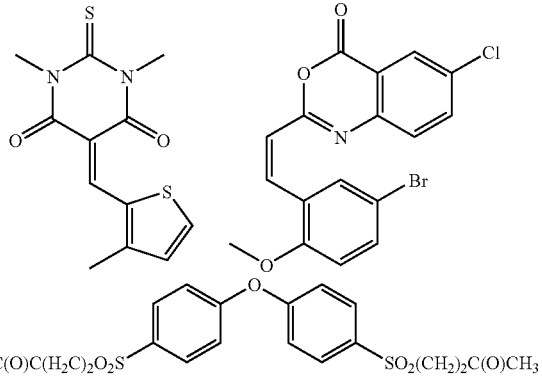
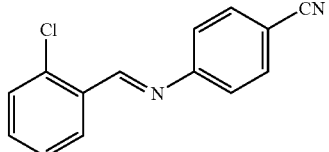
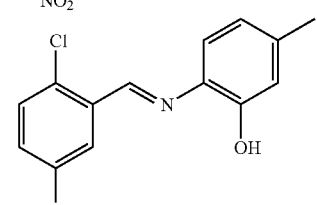
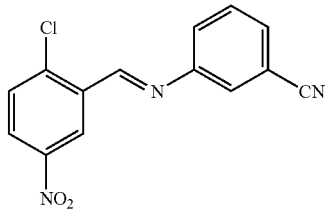
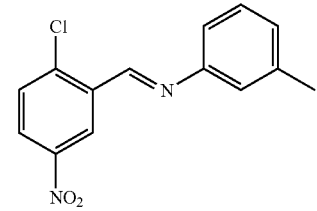
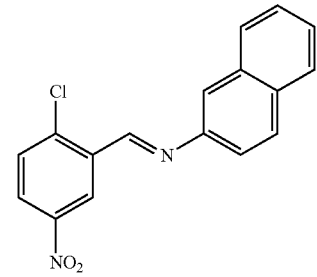
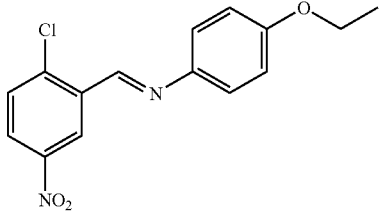

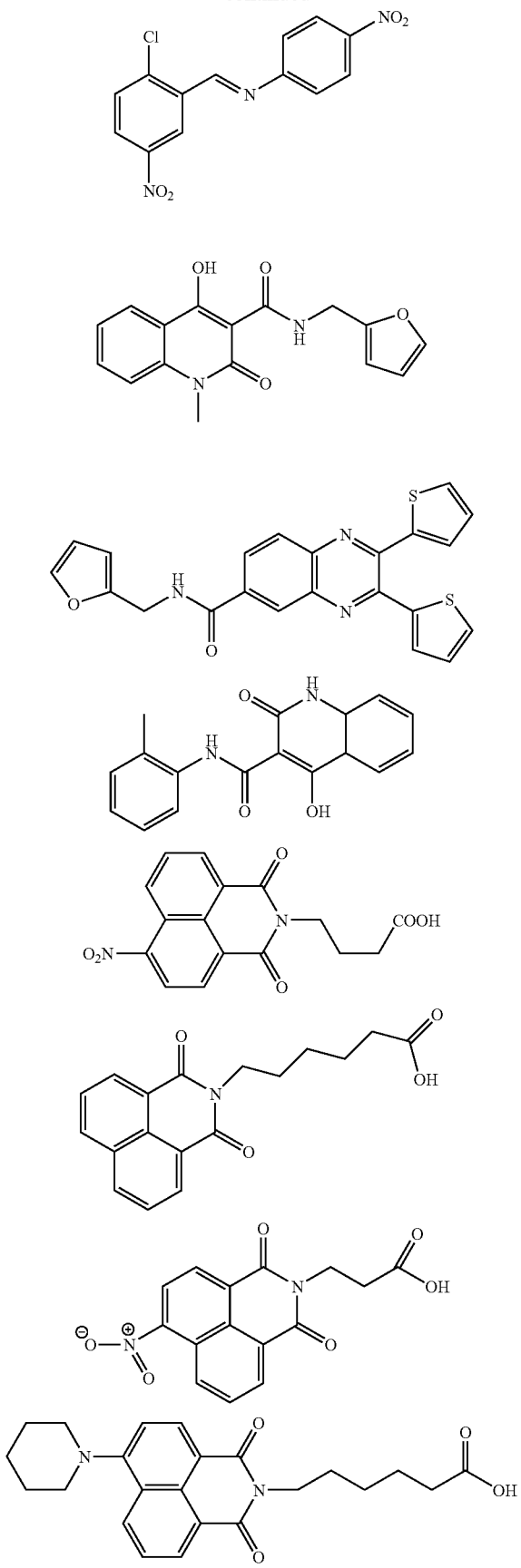
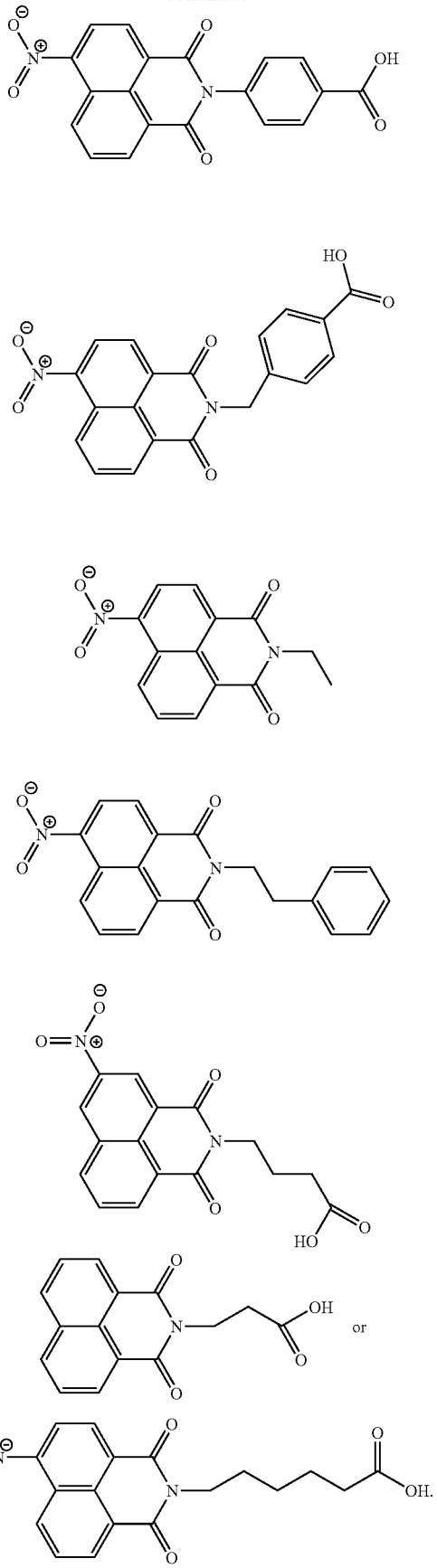

In particular embodiments, the NS1 protein inhibitor is further defined as not any one or more of the following compounds:

-continued

-continued

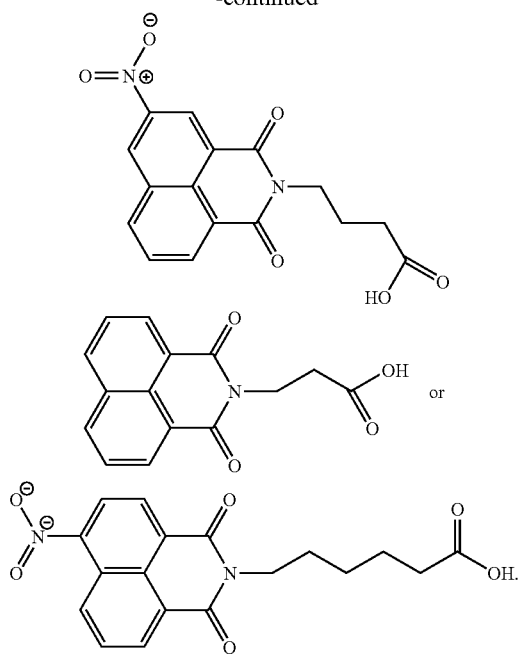

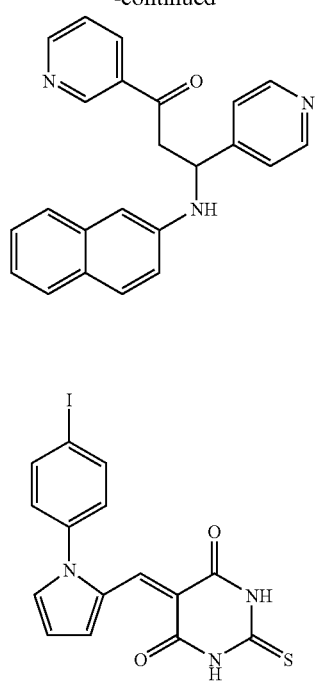

Any one or more of these compounds may optionally be excluded from any generic compound discussed herein, or may optionally be excluded from the class of NS1 protein inhibitors.

Indeed, in particular embodiments, any specific or generic compound discussed herein may be excluded from any embodiment herein. For example, any NS1 protein inhibitor may be further defined as not any of compounds (I), (II), (III), (IV), (V), (VI), (VII), (VIII), (IX), (X), (XI), (XII), and/or (XIII). In certain embodiments, a compound of formula (I), (II), (III), (IV), (V), (VI), (VII), (VIII), (IX), (X), (XI), (XII), and/or (XIII) may be further defined as not any one or more of the following compounds:

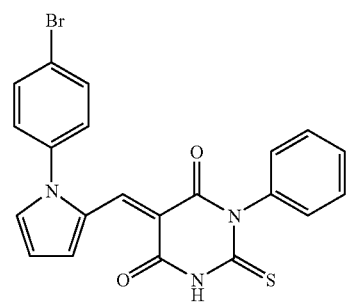

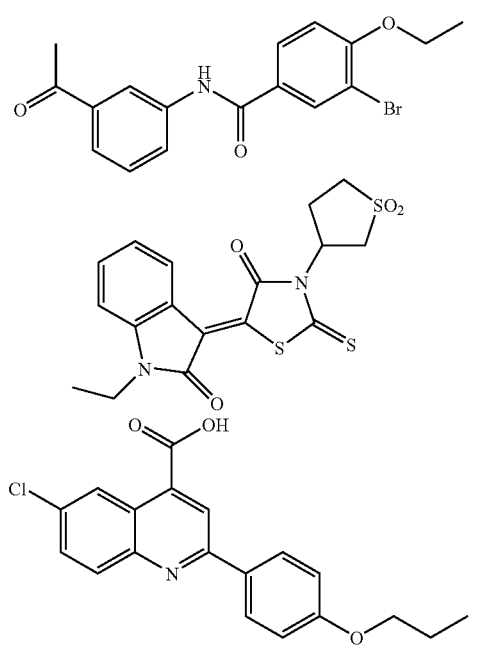

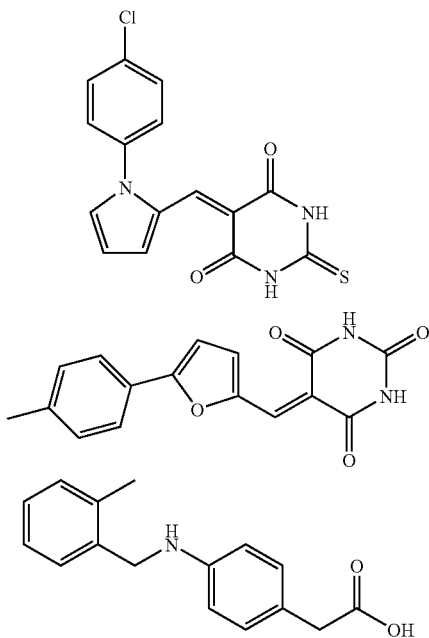

-continued
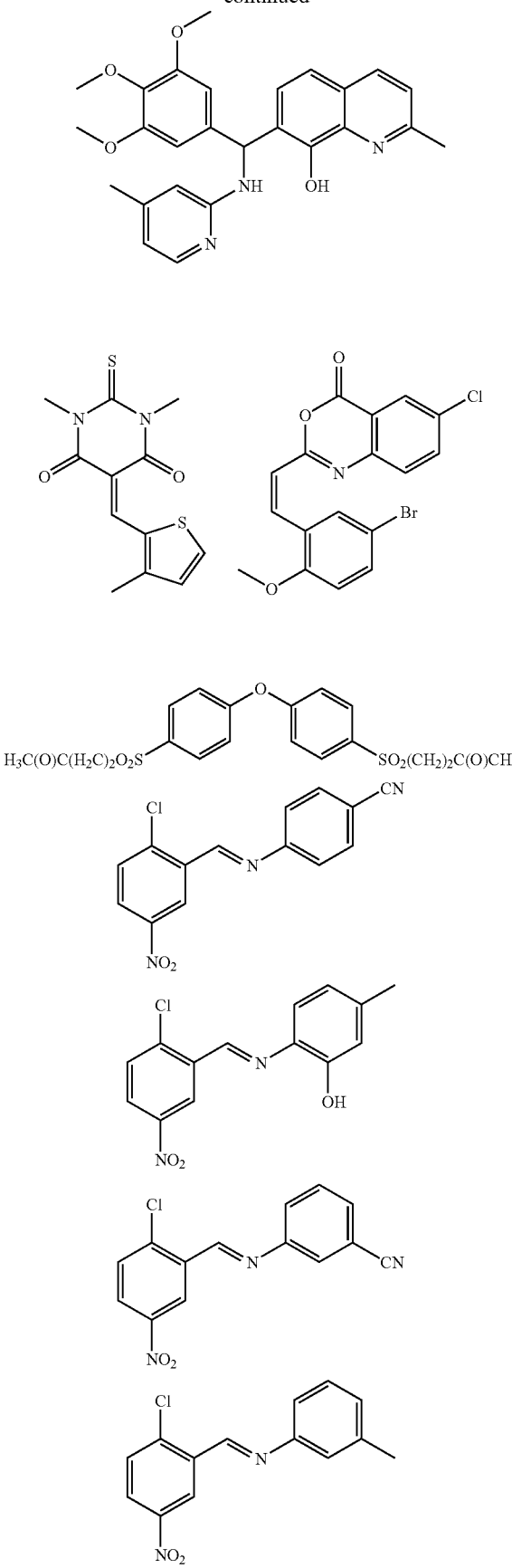
-continued
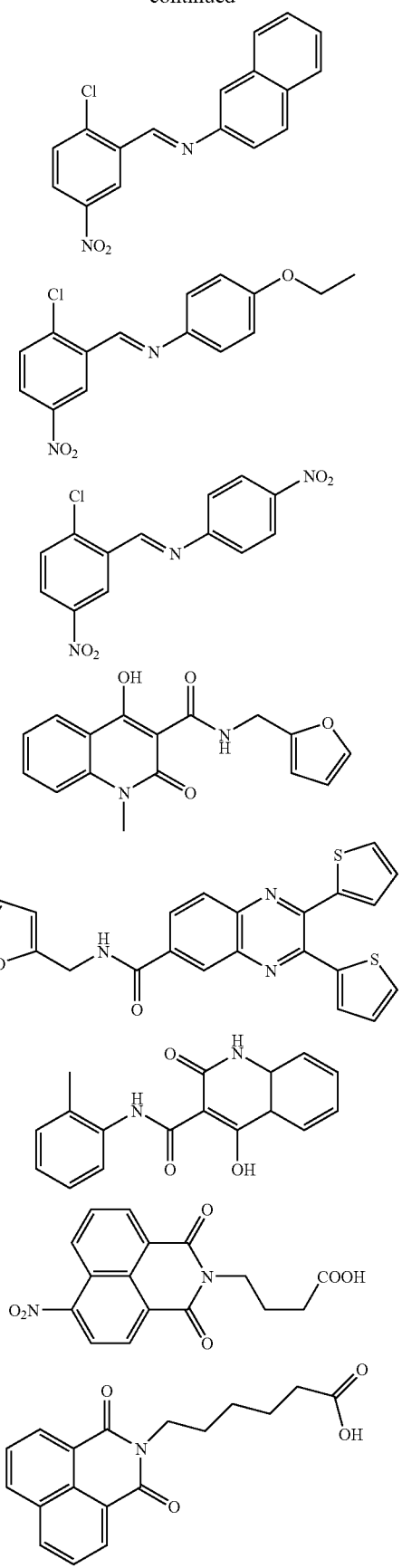

-continued

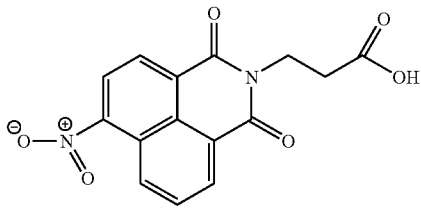
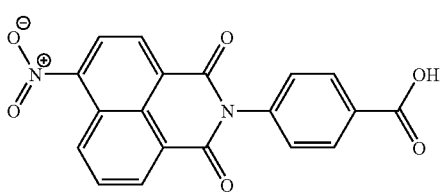
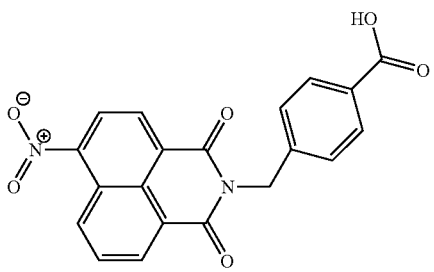
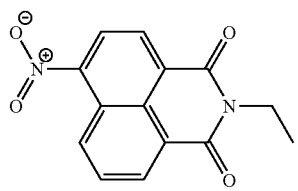
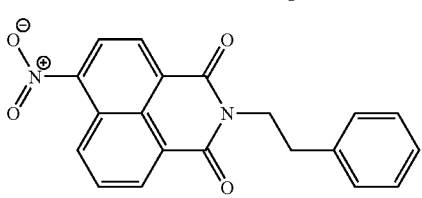
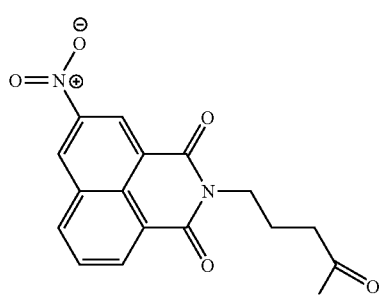

-continued

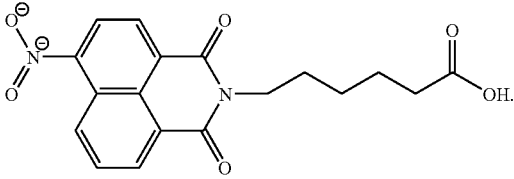

Compounds of the present invention may be administered to a cell, tissue, organism, or patient in any manner known to those of skill in the art. For example, in certain embodiments, an NS1 protein inhibitor may be administered to a patient via a method selected from the group consisting of an inhaled aerosol, a nasal spray, an oral formulation and an injection. The dosage of an NS1 protein inhibitor may also be administered to a cell, tissue, organism, or patient in any manner known to those of skill in the art. In certain embodiments, the dosage ranges from about 1 mg/kg to about 50 mg/kg, or any range derivable therein. In certain embodiments, the dosage ranges from about 10 to about 40 mg/kg. In certain embodiments, the dosage ranges from about 5 to about 45 mg/kg.

Other methods of the present invention contemplate a method of inhibiting NS1 protein comprising administering to a cell an effective amount of an NS1 protein inhibitor. The cell may be in vitro or in vivo.

Yet another method of the present invention contemplates a method of inhibiting influenza A virus cytopathic effect in a cell comprising administering to said cell an effective amount of an NS1 protein inhibitor.

In certain embodiments, a method of reducing the severity or duration of a viral infection in a patient comprising administering to said patient an effective amount of an NS1 protein inhibitor is contemplated. For example, such a method may reduce the severity or duration of viral infection symptoms. The viral infection may be influenza, such as influenza A virus, or any other virus discussed herein. In the case of influenza viruses, such methods may comprise a method of reducing the severity or duration of influenza virus symptoms, such as headache, fever, sore throat, muscle pain, weakness, cough, and/or overall discomfort.

A method of treating or preventing a viral infection in a patient comprising administering to said patient an effective amount of an NS1 protein inhibitor in combination with another agent is another method contemplated by the present invention. In particular embodiments, only methods of treatment are contemplated. The second agent may be, for example, a neuraminidase inhibitor, such as Relenza™ or Tamiflu™, or an M2 proton channel inhibitor, such as amantadine or rimantadine. Methods employing these types of compounds will typically be employed to treat influenza virus infection.

Another method of the present invention contemplates a method of selecting for a compound that inhibits NS1 protein comprising:
 a) infecting a cell with plasmids expressing luciferase and NS1 protein,
 b) contacting the cell with a target compound, and
 c) quantifying the luciferase signal;
wherein a decrease in the luciferase signal relative to the signal obtained in the absence of target compound indicates that the target compound is an NS1 protein inhibitor.

Also encompassed by the present invention are pharmaceutical compositions. Any NS1 protein inhibitor described herein is contemplated as comprised in a pharmaceutical composition. For example, the present invention contemplates pharmaceutical compositions comprising a pharmaceutically acceptable carrier, diluent, and/or excipient and any one or more of the following:
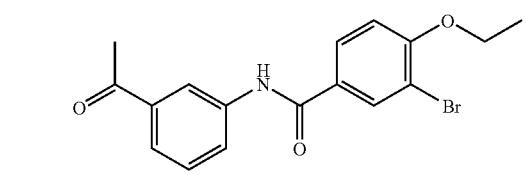
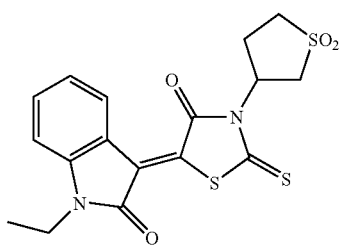
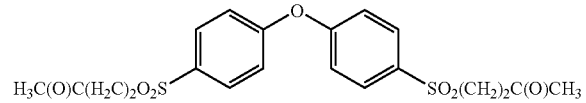
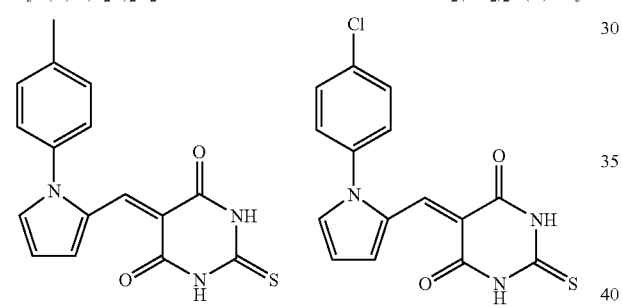
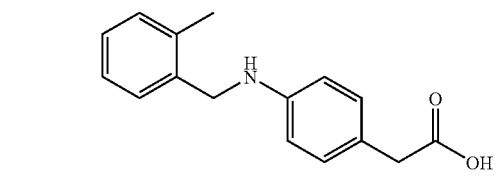
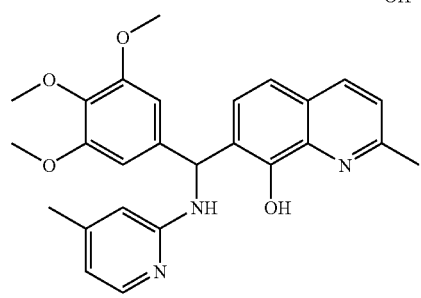
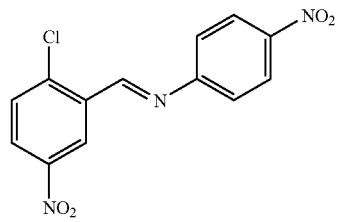
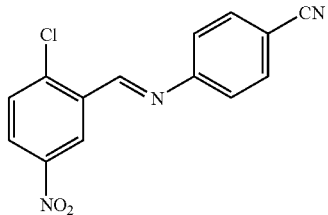
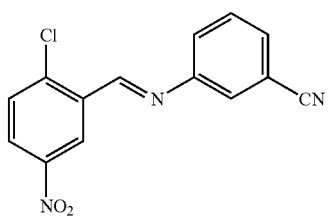
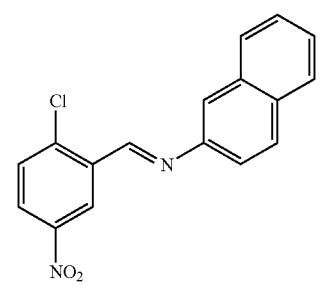
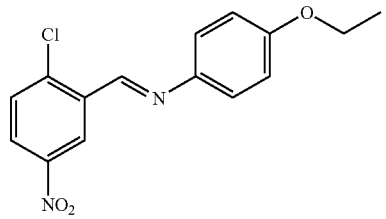
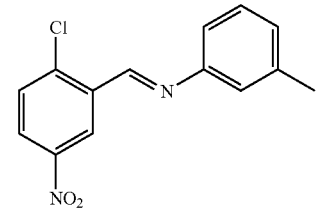
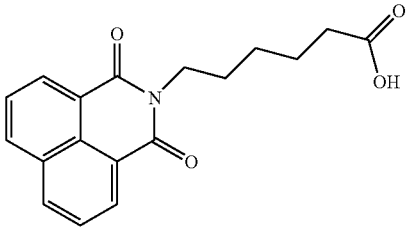
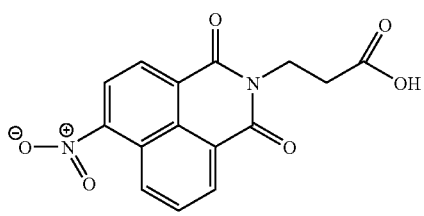

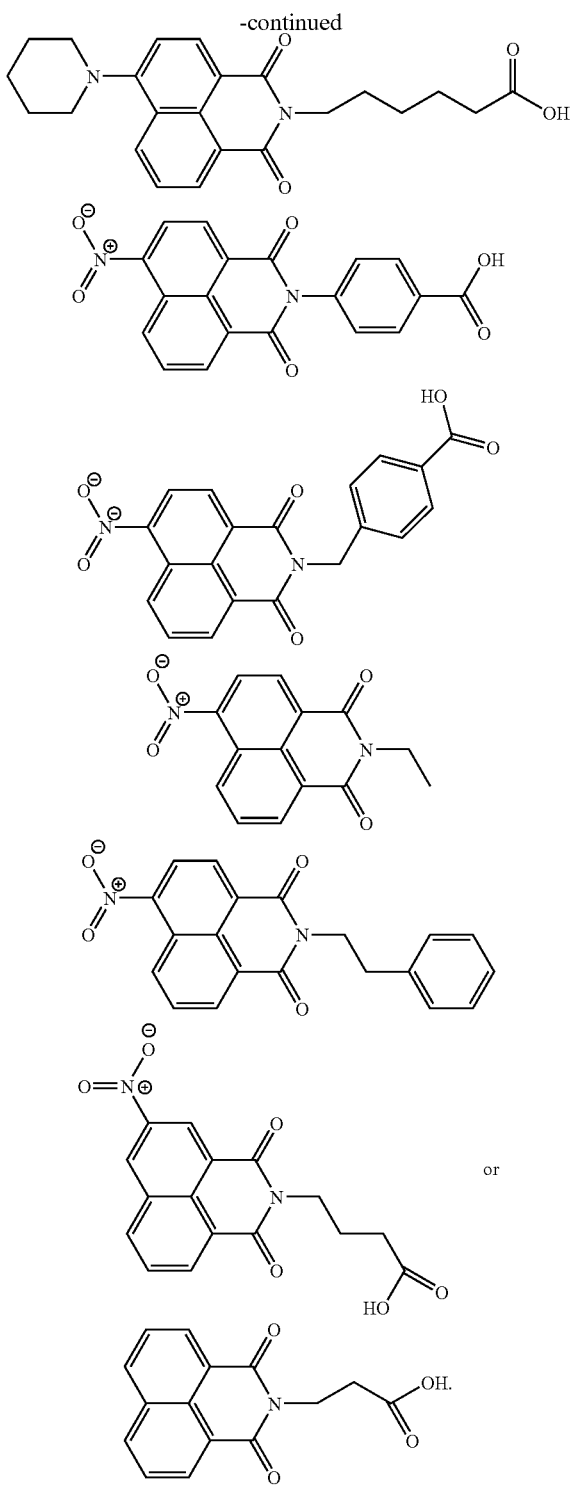

45%, 50%, 55%, 60%, 65%, 70%, 75%, 80%, 85%, 90%, 95%, 99%, or more, or any range derivable therein, reduction of activity compared to normal. In a further example, following administering of a NS1 protein inhibitor, a patient may experience a reduction in severity or duration of one or more viral infection symptoms, such as influenza symptoms as described herein.

The terms "contacted" and "exposed," when applied to a cell, are used herein to describe the process by which a compound of the present invention is administered or delivered to a target cell or are placed in direct juxtaposition with the target cell. The terms "administered" and "delivered" are used interchangeably with "contacted" and "exposed."

As used herein, the term "effective" (e.g., "an effective amount") means adequate to accomplish a desired, expected, or intended result. For example, an "effective amount" may be an amount of a compound sufficient to produce a therapeutic benefit (e.g., effective to reproducibly inhibit decrease, reduce, or otherwise reduce the severity of a viral infection).

"Treatment" and "treating" as used herein refer to administration or application of a therapeutic agent to a subject or performance of a procedure or modality on a subject for the purpose of obtaining a therapeutic benefit of a disease or health-related condition. For example, a subject or patient (e.g., a mammal, such as a human) having a viral infection may be subjected to a treatment comprising administration of a compound of the present invention.

The term "therapeutic benefit" or "therapeutically effective" as used throughout this application refers to anything that promotes or enhances the well-being of the subject with respect to the medical treatment of a condition. This includes, but is not limited to, a reduction in the onset, frequency, duration, or severity of the signs or symptoms of a disease. For example, a therapeutically effective amount of a compound of the present invention (e.g., an NS1 protein inhibitor) may be an amount sufficient to treat or prevent a viral infection.

The term "substantially" and its variations are defined as being largely but not necessarily wholly what is specified as understood by one of ordinary skill in the art, and in one non-limiting embodiment 'substantially' refers to ranges within about 10%, within about 5%, within about 1%, or within about 0.5%. An NS1 protein inhibitor may, for example, be administered to a subject, e.g., a human, suffering from a viral infection until the viral infection has substantially disappeared.

It is specifically contemplated that any limitation discussed with respect to one embodiment of the invention may apply to any other embodiment of the invention. Furthermore, any composition of the invention may be used in any method of the invention, and any method of the invention may be used to produce or to utilize any composition of the invention.

The use of the term "or" in the claims is used to mean "and/or" unless explicitly indicated to refer to alternatives only or the alternative are mutually exclusive, although the disclosure supports a definition that refers to only alternatives and "and/or."

Throughout this application, the term "about" is used to indicate that a value includes the standard deviation of error for the device and/or method being employed to determine the value.

As used herein the specification, "a" or "an" may mean one or more, unless clearly indicated otherwise. As used herein in the claim(s), when used in conjunction with the word "comprising," the words "a" or "an" may mean one or more than one. As used herein "another" may mean at least a second or more.

As used herein, an "NS1 protein inhibitor" is an organopharmaceutical (that is, a small organic molecule) that inhibits NS1 protein activity but does not affect NS1 protein gene expression. NS1 protein inhibitors typically have a molecular weight of about 500 g/mol or less.

The terms "inhibiting," "reducing," or "prevention," or any variation of these terms, when used in the claims and/or the specification, includes any measurable decrease or complete inhibition to achieve a desired result. For example, there may be a decrease of 5%, 10%, 15%, 20%, 25%, 30%, 35%, 40%, Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

The patent or application file contains at least one drawing executed in color. Copies of this patent or patent application publication with color drawing(s) will be provided by the Office upon request and payment of the necessary fee.

FIGS. 1A-1B. Host pathways targeted by NS1 protein. FIG. 1A: Intranuclear pathways—splicing, poly(A) processing, and mRNA export pathways—are connected and inhibited by NS1 protein. The cytoplasmic pathways include the RIG-I pathway. Interaction of NS1 protein with the mRNA export machinery may occur inside the nucleus as in FIG. 1A and at the nuclear pore complex as shown in FIG. 1B. FIG. 1B: Schematic representation of the binding of NS1 protein to key mRNA export factors and the degradation of Nup98, a docking site for mRNA export factors, during influenza virus infection. This inhibition of mRNA export prevents proper expression of mRNAs that encode antiviral proteins. Additional host pathways are targeted by NS1 protein as well (vide infra). VSV M protein binds the Rae1-Nup98 complex, as discussed herein.

FIG. 2A: MDCK cells were mock infected or infected with A/WS/33 Influenza virus at MOI of 1 for 6, 12, and 24 h. Immunofluorescence, using antibodies against influenza proteins (green) and oligo-dT in situ hybridization (red) were performed. FIG. 2B: Expression of Influenza proteins in MDCKs. Cell extracts from MDCK cells infected with A/WS/33 at MOI 1 for the indicated time points, were subjected to immunoblot analysis with anti-influenza protein antibodies.

FIGS. 3A-3H. The NS1 protein of influenza virus interacts with key constituents of the mRNA export pathway. FIG. 3A: Cell lysates from 293T cells were incubated with immobilized recombinant GST or GST-NS1 protein. Bound fractions were analyzed by 4-20% SDS-PAGE followed by immunoblot analysis with antibodies to NXF1, p15, Rae1, E1B-AP5, and Nup98. Numbers on the left depict molecular weight markers. FIGS. 3B and 3C: Experiments were performed as in FIG. 3A except that antibodies against Nup96, Nup62, and Nup153 (mAb414) were used for immunoblot analysis. FIG. 3D: GST-NS1 protein or the amino terminal or carboxyl terminal domains of NS1 protein fused with GST were incubated with cell lysates and processed as in FIG. 3A. FIG. 3E: GST-NS1 protein was incubated with cell lysates untreated or treated with RNase A and processed as in FIG. 3A. FIGS. 3F and 3G: Expression levels of Nups and mRNA export factors in 293T cells (FIG. 3F) and MDCK cells (FIG. 3G) infected with influenza virus. Cell extracts were subjected to immunoblot analysis with antibodies against Nup98, β-actin, Rae1, NXF1, E1B-AP5, and with mAb414 antibodies. FIG. 3H: Half-life measurements of Nup98. MDCK cells were pulse-labeled for 2 hours and chased for the depicted time points. Immunoprecipitations were performed with anti-Nup98 antibodies or pre-immune serum (PI).

FIGS. 4A-4B. The mRNA export inhibition induced by NS1 protein is reverted by increased levels of mRNA export factors. FIG. 4A: Luciferase reporter gene expression assays were performed with 293T cells by co-transfection of reporter plasmids and plasmids encoding NXF1, p15, Rae1, Nup98, and Nup96 as indicated. FIG. 4B: HeLa cells were transfected with a plasmid encoding myc-NS1 protein alone or co-transfected with plasmids encoding myc-NS1 protein, GFP-NXF1 and GFP-p15. Cells were subjected to immunofluorescence with anti-myc antibody (red) followed by oligo-dT in situ hybridization, in blue. Green shows GFP-NXF1 and GFP-p15.

FIGS. 5A-5C. Low levels of Rae1 and Nup98 induce higher susceptibility to influenza virus-mediated cell death and increase in viral replication. FIGS. 5A and 5B: Rae1+/+ Nup98+/+, Rae1+/− Nup98+/+, Rae1+/+ Nup98+/−, and Rae1+/− Nup98+/− mouse embryo fibroblasts (MEFs) were infected with A/WS/33 influenza virus and cell viability was determined by comparing and quantifying bright-field microscopy (gray), DAPI (blue), and exclusion of 2 mM ethidium homodimer-1 (red). FIG. 5C: The number of influenza viral particles was measured in the supernatants of the cells in FIG. 5A: using a hemagglutinin assay.

FIG. 7. The most active compounds identified in the screening assay (see FIG. 6 and Example 6) were verified in the original assay and screened for the ability to block HBEC killing by influenza virus. Examples of certain (8) structural families are shown in FIG. 7. Analogs in the library are related structures which provide structure-activity information. The z score is the compound value minus the experimental mean value divided by the standard deviation of the experimental population.

FIG. 10. Compound 8.3 significantly reverts the mRNA export block induced by influenza virus infection and mediated by NS1. See FIG. 8 for the structure of compound 8.3. FIG. 10A: Oligo-d(T) in situ hybridization was performed to detect poly(A) RNA distribution in the nucleus and in the cytoplasm in uninfected and in MDCK cells infected with WSN (MOI 0.01) for 48 h in the presence or absence of compound 8.3. The image in the left panel shows cells with normal poly(A) distribution whereas the image on the right panel shows both mRNA export blockage (yellow arrows) or normal poly(A) distribution (white arrows). The graph shows the number of cells that presented mRNA export block in infected cells in the absence or presence of 10 μM of compound 8.3. FIG. 10B: Oligo-d(T) in situ hybridization, for detection of poly(A) RNA, in combination with immunofluorescence, for detection of WSN proteins, were performed in the presence or absence of WSN infection at MOI 1 for 12 h and in the presence or absence of compound 8.3 at 50 μM. The results show a significant reversal of mRNA export blockage mediated by influenza virus in the presence of compound 8.3, which allow nuclear export of mRNAs that encode antiviral proteins, therefore, recovering gene expression.

DESCRIPTION OF ILLUSTRATIVE EMBODIMENTS

Figure 2:
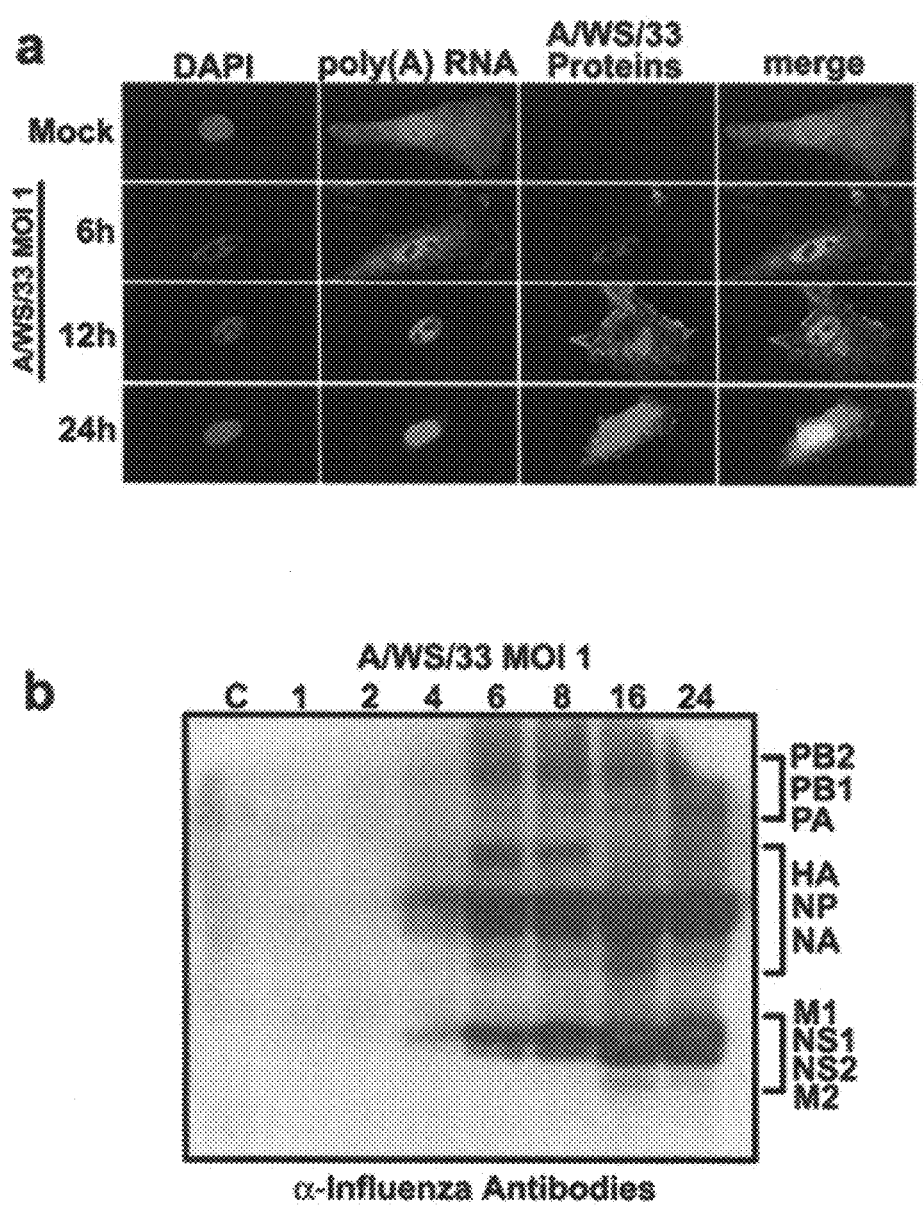
FIGS. 2A-2B. Influenza virus inhibits poly(A) RNA nuclear export.

The influenza NS1 protein inhibits the innate immune response of an infected cell and is required for a pathogenic influenza infection. The present inventors developed an assay for NS1 protein function and screened a library of organopharmaceuticals to identify compounds that blocked NS1 protein function. Active compounds from the first assay were screened in a second assay for virus growth and those that inhibited virus growth were selected for further study. Since NS1 protein is highly conserved across major influenza subtypes and is not a major antigen for generating anti-influenza response, there is no positive selective pressure for natural variants of NS1 protein. This suggests that drugs that target NS1 protein will be broadly effective against influenza subtypes. Indeed, by attenuating the viral infection, the NS1 protein inhibitors described herein may prevent disease while simultaneously allowing an immune response to the infecting strain, thereby giving lasting protection to that particular strain of virus.

A. Influenza

Influenza viruses have been a major cause of mortality and morbidity in man throughout recorded history. Epidemics occur at regular intervals which vary widely in severity but which always cause significant mortality and morbidity, most frequently in the elderly population. The cause of influenza epidemics was first attributed to a virus by R. E. Shops, who showed that influenza epidemics could be transmitted with filtered mucus. Influenza viruses are currently divided into three types: A, B, and C, based upon differences in internal antigenic proteins. Only influenza A viruses are further classified by subtype on the basis of the two main surface glycoproteins hemagglutinin and neuraminidase. Influenza A viruses can infect birds and mammals and a reservoir of virus is maintained in non-human species that cannot be eliminated. It is by crossing species into the human population that new influenza A virus subtypes cause human pandemics. Influenza A subtypes and B viruses are further classified by strains.

New strains of influenza caused by antigenic drift appear at regular frequency, usually annually, and begin a cycle of infection which typically travels around the globe. Approximately every year, at least one minor change occurs in either the hemagglutinin or neuraminidase antigens (or both), but that change is sufficient to render those persons who had a previous strain susceptible to the new strain. As influenza is caused by a variety of species and strains of viruses, in any given year some strains can die out while others create epidemics while yet another strain can cause a pandemic. Little is known about how individual epidemics are initiated. Non-limiting exemplary strains include A/Wisconsin/67/2005 (H3N2)-like virus (A/Wisconsin/67/2005 or A/Hiroshima/52/2005 strains), A/New Caledonia/20/99 (H1N1), B/Malaysia/2506/2004-like virus (B/Malaysia/2506/2004 or B/Ohio/1/2005 strains), and A/Solomon Islands/3/2006 (H1N1)-like virus.

An influenza infection produces an acute set of symptoms including headache, fever, sore throat, muscle pain, weakness, cough, and/or overall discomfort. In severe cases or situations involving pre-existing pulmonary or cardiovascular disease, hospitalization is required. Pneumonia due to direct viral infection or due to secondary bacterial or viral invasion is the most frequent complication. For a review on the clinical aspects of influenza virus infection, see Douglas, 1990.

B. Influenza A Virus

The genome of the influenza A virus consists of 8 negative single-strand RNA segments that encode 10 genes necessary for viral replication and virulence (Knipe and Howley, 2001).

Influenza viruses are unusual among negative strand RNA viruses in that they replicate in the nucleus of the cell unlike others that display a predominantly or exclusively cytoplasmic life cycle. This feature has led to the evolution of additional complexities in the influenza virus life cycle and in its interaction with its host's cellular machinery. These complexities present potential vulnerabilities that might be exploited for therapeutic benefit.

Similar to most viral infections, replication of influenza virus in vertebrate cells is recognized by elements of the innate immune system, triggering a signal transduction pathway leading to type I IFN production and response. If fully functional, the type I IFN pathway would produce a potent antiviral state through induction of a large battery of antiviral effector proteins that preclude further viral replication. However, like many evolutionarily successful viruses, influenza virus has evolved mechanisms for inhibiting this innate response (Guo et al., 2006; Levy DE and Garcia-Sastre, 2001; Li et al., 2006; Mibayashi et al., 2006; Min and Krug, 2006; Opitz et al., 2006; Pichlmair et al., 2006), mainly through functions of the NS1 protein, described below (Garcia-Sastre et al., 1998). Negative strand RNA viruses induce innate immunity by two cellular pathways, a cytoplasmic recognition pathway that operates in most cell types, and a transmembrane pathway that operates predominantly in dendritic and monocytic cells. Both pathways can trigger type I IFN gene transcription through activation of latent transcription factors of the IRF and NF-κB families. However, genetic evidence suggests that the cytoplasmic pathway predominates for protection against influenza viral infections and that the transmembrane pathway may in fact exacerbate infection (Guillot et al., 2005; Le Goffic et al., 2006; Le Goffic et al., 2007).

The cytoplasmic signaling pathway operates in the primary targets for respiratory viral infections, bronchial and pulmonary epithelial cells and alveolar macrophages. This signal transduction pathway is triggered by recognition of viral RNA or ribonucleoprotein particles (RNP) by the cytoplasmic RNA helicase RIG-I (Guo et al., 2006; Mibayashi et al., 2006; Opitz et al., 2006; Pichlmair et al., 2006) leading to activation of the downstream adaptor and effector proteins, MAVS (also known as IPS-1, VISA, or Cardif), TBK-1 (also known as T2K or NAK), IKK-ε (also known as IKK-i), IRF3, and IRF7 (Akira et al., 2006; Kawai and Akira, 2006). Activated IRF3, in conjunction with activated NF-kB and AP-1 transcription factors, is essential for induction of IFN-β gene expression, while activated IRF7 mediates most IFN-α gene expression (Akira et al., 2006; Kawai and Akira, 2006; Marie et al., 1998). Because IRF7 and many other components of the signaling pathway are expressed at low levels in epithelial cells until induced in response to an initial IFN stimulation, IFN-α gene expression is highly dependent on positive feedback through the IFN response pathway (Marie et al., 1998; Taniguchi and Takaoka, 2001). Compounds of the present invention may trigger IFN-β and/or IFN-α gene expression. See Enniga, 2002.

C. Interferons

As noted above, NS1 protein inhibits interferon (IFN) gene induction and IFN-modulated immune responses. As such, the NS1 protein inhibitors described herein are also novel inhibitors of viral replication and pathogenesis that act by preventing NS1 protein-mediated inhibition of IFN-dependent immune responses to viral infection.

Interferons are important cytokines characterized by antiviral, antiproliferative and immunomodulatory activities.

Interferons are proteins that alter and regulate the transcription of genes within a cell by binding to interferon receptors on the regulated cell's surface, thereby preventing viral replication within the cells. There are several groups of interferons (IFN), including α (formerly $α_1$), Ω (formerly $α_2$), β, γ and τ. Mature human interferons are between 165 and 172 amino acids in length. In humans IFN-α and IFN-Ω are encoded by multiple, closely related non-allelic genes. Additionally, there are pseudo-genes of IFN-α and IFN-Ω. By contrast, IFN-β and IFN-γ are encoded by unique genes.

The interferons can also be grouped into two types. IFN-γ is the sole type II interferon; all others are type I interferons. Type I and type II interferons differ in gene structure (type II interferon genes have three exons; type I, one), chromosome location (in humans, type II is located on chromosome-12; the type I interferon genes are linked and on chromosome-9), and the types of tissues where they are produced (type I interferons are synthesized ubiquitously, type II by lymphocytes). Type I interferons competitively inhibit each others binding to cellular receptors, while type II interferon has a distinct receptor (reviewed by Sen and Lengyel, 1992).

IFN-α has become most widely used for therapeutic purposes. Among the interferons of human origin, the IFN-αs are divided into several subtypes, which are either encoded by different gene loci or alleles of those. The function of each subtype is still not clear, and the molecular or cellular targets of their antiviral and antineoplastic activities is thus not fully investigated. Human IFN-αs are encoded by a multigene family consisting of about 20 genes; each gene encodes a single subtype of the human IFN-α. Human IFN-α polypeptides are produced by a number of human cell lines and human leukocyte cells after exposure to viruses or double-stranded RNA, or in transformed leukocyte cell lines (e.g., lymphoblastoid lines). IFN-αs interact with cell-surface receptors and induce the expression, primarily at the transcriptional level, of a broad but specific set of cellular genes. Several IFN-α-induced gene products have been used as markers for the biological activity of interferons. These include, for instance, ISG15, ISG54, IRF1, GBP, and IP10.

Human IFN-β is a regulatory polypeptide with a molecular weight of 22 kDa consisting of 166 amino acid residues. It can be produced by most cells in the body, in particular fibroblasts, in response to viral infection or exposure to other biologics. It binds to a multimeric cell surface receptor, and productive receptor binding results in a cascade of intracellular events leading to the expression of IFN-β inducible genes which, in turn, produces effects which can be classified as antiviral, antiproliferative, or immunomodulatory.

D. NS1 Protein

The nonstructural NS1 proteins of pathogenic strains of influenza virus are major virulence factors for viral pathogenesis. NS1 protein inhibits host gene expression and signal transduction required to mount innate and adaptive immune responses. In infected cells, NS1 protein is localized in the nucleus and the cytoplasm. The nuclear pool of NS1 protein inhibits mRNA processing and nuclear export of mRNAs, preventing proper expression of antiviral genes, while the cytoplasmic pool inhibits signal transduction pathways necessary for antiviral gene induction and effector proteins necessary for antiviral defense. Genetic studies have shown that abrogation of NS1 protein functions by mutation results in highly attenuated viruses that can only replicate in immunocompromised hosts (Garcia-Sastre et al., 1998; Krug et al., 2003). For example, in animals or cells deficient in type I IFN responses, influenza viral mutants lacking NS1 protein replicate at near wild type levels and cause diseases similar to wild type viruses (Garcia-Sastre et al., 1998). These observations define NS1 protein as an essential element of viral virulence and suggest that its importance for viral pathogenesis is to selectively debilitate innate immunity.

Inhibition of either the primary activation or the secondary viral response pathways in cells described above in section A severely impairs innate immune responses by blocking IFN protection, and it is in this manner that NS1 protein promotes virulence. NS1 protein inhibits IRF3 and NF-κB activation and therefore IFN gene induction by interfering with the cytoplasmic signal transduction pathway (Donelan et al., 2004; Talon et al., 2000) through inhibiting the function of RIG-I (Guo et al., 2006; Mibayashi et al., 2006; Opitz et al., 2006; Pichlmair et al., 2006). NS1 protein also prevents IFN action by sequestering double-stranded RNA and/or targeting the function of downstream antiviral effector proteins, such as PKR and the RNase L pathway (Li et al., 2006; Min and Krug, 2006).

NS1 protein is a 230-amino acid protein that contains two major domains and forms a homodimer (Knipe and Howley, 2001). The amino terminal region of NS1 protein (residues 1-73) encompasses an RNA-binding domain that is able to interact non-specifically with dsRNA (Knipe and Howley, 2001). Structural and biochemical studies have shown that arginine-38 (R38) is required for binding dsRNA. This interaction is of low affinity compared to other RNA binding proteins; nevertheless, recent studies of mutant influenza viruses with impaired dsRNA binding ability have demonstrated that this function contributes to virulence. Mutations of NS1 protein that abrogate dsRNA binding resulted in attenuated viruses that grow to lower titers, induced increased IFN production, and failed to effectively block antiviral effector functions (Donelan et al., 2003; Min and Krug, 2006). However, abrogation of RNA binding attenuates virulence less than complete loss of the NS1 protein. Thus, additional sequences of the NS1 protein are also critical for virulence. A region within the amino terminal domain of NS1 protein, from amino acids 19 to 38, is required for NS1 protein-mediated inhibition of mRNA nuclear export (Qian et al., 1994), which, as mentioned below, is a key nuclear function of NS1 protein that inhibits expression of host antiviral genes. In fact, the present inventors have recently shown that the amino terminal domain of NS1 protein is involved in its interaction with the mRNA export machinery, namely the NXF1-p15 heterodimer, Rae1 and E1B-AP5 (Satterly et al., 2007), which are mRNA export factors known to form a complex and to mediate nuclear exit of mRNAs (Bachi et al., 2000; Blevins et al., 2003; Satterly et al., 2007).

The carboxyl terminal domain of NS1 protein, amino acids 134 to 161, is also required for the inhibitory effect of NS1 protein on mRNA nuclear export (Qian et al., 1994). The carboxy terminus of NS1 protein is also termed the effector domain and is the region that binds the human 30 kD subunit of the cleavage and polyadenylation specificity factor (CPSF) and the poly(A)-binding protein II (PABII), which are involved in binding the AAUAAA polyadenylation signal and in the elongation of the poly(A) chain, respectively (Chen et al., 1999; Nemeroff et al., 1998). The interaction of NS1 protein with these proteins inhibits 3' end processing of host mRNAs and contributes to nuclear retention of host mRNAs. A mutant influenza virus that expresses an NS1 protein with a mutated CPSF binding site is highly attenuated and cells infected with this virus produce high levels of IFNβ mRNA (Noah et al., 2003; Twu et al., 2006). These effects are also likely caused by changes in interactions between the mutant NS1 protein and additional host proteins directly involved in nuclear export of mRNAs, as the inventors demonstrate herein. mRNA processing and export are connected—some proteins remain bound to mRNAs throughout these processes and others are exchanged with factors specific for each step. In fact, combinatorial assembly of complexes that share some common factors are being revealed as mechanisms to generate specific functions and/or redundancy (Rochette-Egly, 2005).

The present inventors have found that NS1 protein binds cellular factors involved in nuclear export of bulk mRNAs, while viral mRNAs exit the nucleus via a distinct pathway. This inhibition of mRNA export can be reverted by increased expression of the mRNA export factors targeted by NS1 protein. In contrast, cells from mice that express low levels of specific mRNA export factors are highly permissive to influenza virus replication and pathogenesis. Similarly, the cytoplasmic pool of NS1 protein inhibits IFN gene induction by interfering with the signal transduction pathway triggered by viral infection. In the absence of this NS1 protein-imposed block, viral replication is highly attenuated and pathogenesis is reduced, except in mice with mutations in elements normally targeted by NS1 protein. Compounds of the present invention may inhibit only nuclear and/or both nuclear and cytoplasmic NS1 protein functions.

E. Chemical Definitions

As used herein, the term "amino" means $-NH_2$; the term "nitro" means $-NO_2$; the term "halo" or "halogen" designates —F, —Cl, —Br or —I; the term "thiol" means —SH; the term "cyano" means —CN; and the term "hydroxy" means —OH.

The term "alkyl" includes straight-chain alkyl, branched-chain alkyl, cycloalkyl (alicyclic), cyclic alkyl, heteroatom-unsubstituted alkyl, heteroatom-substituted alkyl, heteroatom-unsubstituted $C_n$-alkyl, and heteroatom-substituted $C_n$-alkyl. In certain embodiments, lower alkyls are contemplated. The term "lower alkyl" refers to alkyls of 1-6 carbon atoms (that is, 1, 2, 3, 4, 5 or 6 carbon atoms). The term "heteroatom-unsubstituted $C_n$-alkyl" refers to a radical, having a linear or branched, cyclic or acyclic structure, further having no carbon-carbon double or triple bonds, further having a total of n carbon atoms, all of which are nonaromatic, 3 or more hydrogen atoms, and no heteroatoms. For example, a heteroatom-unsubstituted $C_1$-$C_{10}$-alkyl has 1 to 10 carbon atoms. The groups, $-CH_3$ (Me), $-CH_2CH_3$ (Et), $-CH_2CH_2CH_3$ (n-Pr), $-CH(CH_3)_2$ (iso-Pr), $-CH(CH_2)_2$ (cyclopropyl), $-CH_2CH_2CH_2CH_3$ (n-Bu), $-CH(CH_3)CH_2CH_3$ (sec-butyl), $-CH_2CH(CH_3)_2$ (iso-butyl), $-C(CH_3)_3$ (tert-butyl), $-CH_2C(CH_3)_3$ (neo-pentyl), cyclobutyl, cyclopentyl, and cyclohexyl, are all non-limiting examples of heteroatom-unsubstituted alkyl groups. The term "heteroatom-substituted $C_n$-alkyl" refers to a radical, having a single saturated carbon atom as the point of attachment, no carbon-carbon double or triple bonds, further having a linear or branched, cyclic or acyclic structure, further having a total of n carbon atoms, all of which are nonaromatic, 0, 1, or more than one hydrogen atom, at least one heteroatom, wherein each heteroatom is independently selected from the group consisting of N, O, F, Cl, Br, I, Si, P, and S. For example, a heteroatom-substituted $C_1$-$C_{10}$-alkyl has 1 to 10 carbon atoms. The following groups are all non-limiting examples of heteroatom-substituted alkyl groups: trifluoromethyl, $-CH_2F$, $-CH_2Cl$, $-CH_2Br$, $-CH_2OH$, $-CH_2OCH_3$, $-CH_2OCH_2CF_3$, $-CH_2OC(O)CH_3$, $-CH_2NH_2$, $-CH_2NHCH_3$, $-CH_2N(CH_3)_2$, $-CH_2CH_2Cl$, $-CH_2CH_2OH$, $CH_2CH_2OC(O)CH_3$, $-CH_2CH_2NHCO_2C(CH_3)_3$, and $-CH_2Si(CH_3)_3$.

The term "alkoxy" includes straight-chain alkoxy, branched-chain alkoxy, cycloalkoxy, cyclic alkoxy, heteroatom-unsubstituted alkoxy, heteroatom-substituted alkoxy, heteroatom-unsubstituted $C_n$-alkoxy, and heteroatom-substituted $C_n$-alkoxy. In certain embodiments, lower alkoxys are contemplated. The term "lower alkoxy" refers to alkoxys of 1-6 carbon atoms (that is, 1, 2, 3, 4, 5 or 6 carbon atoms). The term "heteroatom-unsubstituted $C_n$-alkoxy" refers to a group, having the structure —OR, in which R is a heteroatom-unsubstituted $C_n$-alkyl, as that term is defined above. Heteroatom-unsubstituted alkoxy groups include: $-OCH_3$, $-OCH_2CH_3$, $-OCH_2CH_2CH_3$, $-OCH(CH_3)_2$, and $-OCH(CH_2)_2$. The term "heteroatom-substituted $C_n$-alkoxy" refers to a group, having the structure —OR, in which R is a heteroatom-substituted $C_n$-alkyl, as that term is defined above. For example, $-OCH_2CF_3$ is a heteroatom-substituted alkoxy group.

Modifications or derivatives of the compounds, agents, and active ingredients disclosed throughout this specification are contemplated as being useful with the methods and compositions of the present invention. Derivatives may be prepared and the properties of such derivatives may be assayed for their desired properties by any method known to those of skill in the art.

In certain aspects, "derivative" refers to a chemically-modified compound that still retains the desired effects of the compound prior to the chemical modification. An "NS1 protein inhibitor derivative," therefore, refers to a chemically modified compound that still retains the desired effects of the parent NS1 protein inhibitor prior to its chemical modification. Such effects may be enhanced (e.g., slightly more effective, twice as effective, etc.) or diminished (e.g., slightly less effective, 2-fold less effective, etc.) relative to the parent NS1 protein inhibitor, but may still be considered an NS1 protein inhibitor derivative. Such derivatives may have the addition, removal, or substitution of one or more chemical moieties on the parent molecule. Non-limiting examples of the types of modifications that can be made to the compounds and structures disclosed herein include the addition or removal of lower unsubstituted alkyls such as methyl, ethyl, propyl, or substituted lower alkyls such as hydroxymethyl or aminomethyl groups; carboxyl groups and carbonyl groups; hydroxyls; nitro, amino, amide, imide, and azo groups; sulfate, sulfonate, sulfono, sulfhydryl, sulfenyl, sulfonyl, sulfoxido, sulfonamide, phosphate, phosphono, phosphoryl groups, and halide substituents. Additional modifications can include an addition or a deletion of one or more atoms of the atomic framework, for example, substitution of an ethyl by a propyl; substitution of a phenyl by a larger or smaller aromatic group. Alternatively, in a cyclic or bicyclic structure, heteroatoms such as N, S, or O can be substituted into the structure instead of a carbon atom.

Prodrugs and solvates of the compounds of the present invention are also contemplated herein. The term "prodrug" as used herein, is understood as being a compound which, upon administration to a subject, such as a mammal, undergoes chemical conversion by metabolic or chemical processes to yield a compound any of the formulas herein, or a salt and/or solvate thereof (Bundgaard, 1991; Bundgaard, 1985). Solvates of the compounds of the present invention are preferably hydrates.

The term "pharmaceutically acceptable salts," as used herein, refers to salts of compounds of this invention that are substantially non-toxic to living organisms. Typical pharmaceutically acceptable salts include those salts prepared by reaction of a compound of this invention with an inorganic or organic acid, or an organic base, depending on the substituents present on the compounds of the invention.

Non-limiting examples of inorganic acids which may be used to prepare pharmaceutically acceptable salts include: hydrochloric acid, phosphoric acid, sulfuric acid, hydrobromic acid, hydroiodic acid, phosphorous acid and the like. Examples of organic acids which may be used to prepare pharmaceutically acceptable salts include: aliphatic mono- and dicarboxylic acids, such as oxalic acid, carbonic acid, citric acid, succinic acid, phenyl-heteroatom-substituted alkanoic acids, aliphatic and aromatic sulfuric acids and the like. Pharmaceutically acceptable salts prepared from inorganic or organic acids thus include hydrochloride, hydrobromide, nitrate, sulfate, pyrosulfate, bisulfate, sulfite, bisulfate, phosphate, monohydrogenphosphate, dihydrogenphosphate, metaphosphate, pyrophosphate, hydroiodide, hydrofluoride, acetate, propionate, formate, oxalate, citrate, lactate, p-toluenesulfonate, methanesulfonate, maleate, and the like.

Suitable pharmaceutically acceptable salts may also be formed by reacting the agents of the invention with an organic base such as methylamine, ethylamine, ethanolamine, lysine, ornithine and the like.

Pharmaceutically acceptable salts include the salts formed between carboxylate or sulfonate groups found on some of the compounds of this invention and inorganic cations, such as sodium, potassium, ammonium, or calcium, or such organic cations as isopropylammonium, trimethylammonium, tetramethylammonium, and imidazolium.

It should be recognized that the particular anion or cation forming a part of any salt of this invention is typically not critical, so long as the salt, as a whole, is pharmacologically acceptable. Additional examples of pharmaceutically acceptable salts and their methods of preparation and use are presented in *Handbook of Pharmaceutical Salts: Properties, Selection and Use* (2002), which is incorporated herein by reference.

As used herein, "protecting group" refers to a moiety attached to a functional group to prevent an otherwise unwanted reaction of that functional group. The term "functional group" generally refers to how persons of skill in the art classify chemically reactive groups. Examples of functional groups include hydroxyl, amine, sulfhydryl, amide, carboxyls, carbonyls, etc. Protecting groups are well-known to those of skill in the art. Non-limiting exemplary protecting groups fall into categories such as hydroxy protecting groups, amino protecting groups, sulfhydryl protecting groups and carbonyl protecting groups. Such protecting groups may be found in Greene and Wuts, 1999. The NS1 protein inhibitors described herein are also contemplated as protected by one or more protecting groups.

Compounds of the present invention may contain one or more asymmetric centers and thus can occur as racemates and racemic mixtures, single enantiomers, diastereomeric mixtures and individual diastereomers. In certain embodiments, a single diastereomer is present. All possible stereoisomers of the compounds of the present invention are contemplated as being within the scope of the present invention. However, in certain aspects, particular diastereomers are contemplated. The chiral centers of the compounds of the present invention can have the S- or the R-configuration, as defined by the IUPAC 1974 Recommendations. In certain aspects, certain compounds of the present invention may comprise S- or R-configurations at particular carbon centers.

Compounds of the present invention may be purchased, such as SigmaAldrich (Milwaukee, Wis.); Chemical Diversity Laboratories (San Diego, Calif.); and ChemBridge Corp. (San Diego, Calif.). Compounds may also be ordered from companies that prepare customized organic compounds (e.g., AsisChem, Inc., SynChem, Inc.), or prepared using synthetic organic techniques. For example, the scheme below depicts one means of synthetically accessing certain NS1 inhibitors of the present invention:

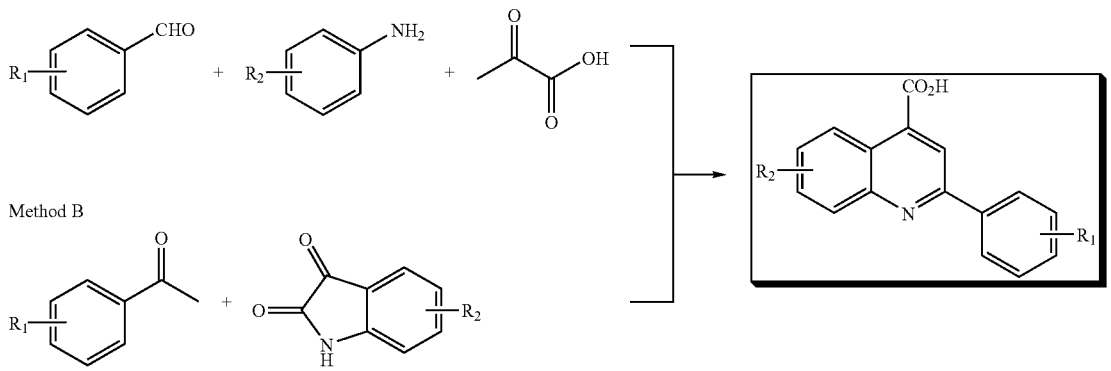

Other methods of preparing certain compounds of the present invention include the following:

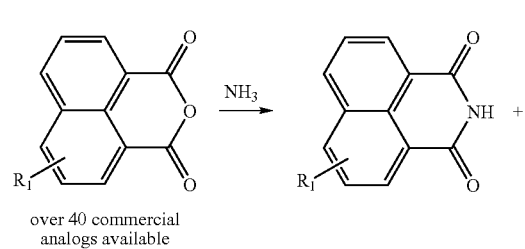

over 40 commercial analogs available

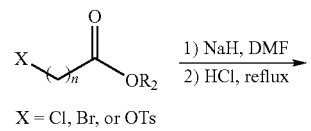

X = Cl, Br, or OTs

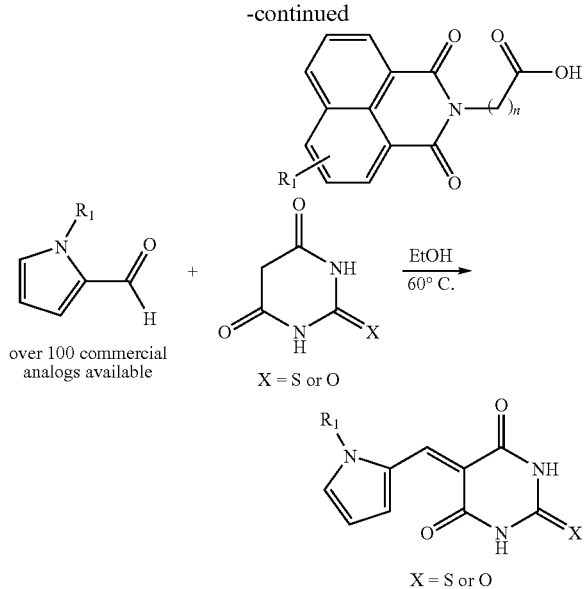

Other synthetic techniques to prepare compounds of the present invention as well as derivatives are well-known to those of skill in the art. For example, Smith and March, 2001 discuss a wide variety of synthetic transformations, reaction conditions, and possible pitfalls relating thereto. Methods discussed therein may be adapted to prepare compounds of the present invention from commercially available starting materials.

Solvent choices for preparing compounds of the present invention will be known to one of ordinary skill in the art. Solvent choices may depend, for example, on which one(s) will facilitate the solubilizing of all the reagents or, for example, which one(s) will best facilitate the desired reaction (particularly when the mechanism of the reaction is known). Solvents may include, for example, polar solvents and non-polar solvents. Solvents choices include, but are not limited to, tetrahydrofuran, dimethylformamide, dimethylsulfoxide, dioxane, methanol, ethanol, hexane, methylene chloride and acetonitrile. More than one solvent may be chosen for any particular reaction or purification procedure. Water may also be admixed into any solvent choice. Further, water, such as distilled water, may constitute the reaction medium instead of a solvent.

Persons of ordinary skill in the art will be familiar with methods of purifying compounds of the present invention. One of ordinary skill in the art will understand that compounds of the present invention can generally be purified at any step, including the purification of intermediates as well as purification of the final products. In preferred embodiments, purification is performed via silica gel column chromatography or HPLC.

In view of the above definitions, other chemical terms used throughout this application can be easily understood by those of skill in the art. Terms may be used alone or in any combination thereof.

F. Pharmaceutical Formulations and Routes for Administration

Pharmaceutical compositions of the present invention comprise an effective amount of one or more candidate substances (e.g., an NS1 protein inhibitor) or additional agents dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of a pharmaceutical composition that contains at least one candidate substance or additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, pp 1289-1329, 1990). Except insofar as any conventional carrier is incompatible with the active ingredient, its use in the therapeutic or pharmaceutical compositions is contemplated.

The candidate substance may comprise different types of carriers depending on whether it is to be administered in solid, liquid or aerosol form, and whether it need to be sterile for such routes of administration as injection. The present invention can be administered intravenously, intraarterially, intraperitoneally, intracranially, intrapleurally, intratracheally, intranasally (e.g., via a nasal spray), topically, subcutaneously, intravesicularlly, mucosally, orally, locally, via inhalation (e.g., aerosol inhalation), via injection, via infusion, via continuous infusion, via localized perfusion bathing target cells directly, via a catheter, via a lavage, in cremes, in lipid compositions (e.g., liposomes), or by other method or any combination of the foregoing as would be known to one of ordinary skill in the art (see, for example, Remington's Pharmaceutical Sciences, 1990).

In particular embodiments, the composition is administered to a subject using a drug delivery device. Any drug delivery device is contemplated for use in delivering a pharmaceutically effective amount of an NS1 protein inhibitor.

The actual dosage amount of a composition of the present invention administered to an animal patient can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

The dose can be repeated as needed as determined by those of ordinary skill in the art. Thus, in some embodiments of the methods set forth herein, a single dose is contemplated. In other embodiments, two or more doses are contemplated. Where more than one dose is administered to a subject, the time interval between doses can be any time interval as determined by those of ordinary skill in the art. For example, the time interval between doses may be about 1 hour to about 2 hours, about 2 hours to about 6 hours, about 6 hours to about 10 hours, about 10 hours to about 24 hours, about 1 day to about 2 days, about 1 week to about 2 weeks, or longer, or any time interval derivable within any of these recited ranges.

In certain embodiments, it may be desirable to provide a continuous supply of a pharmaceutical composition to the patient. This could be accomplished by catheterization, followed by continuous administration of the therapeutic agent. The administration could be intra-operative or post-operative.

In certain embodiments, pharmaceutical compositions may comprise, for example, at least about 0.1% of an NS1 protein inhibitor. In other embodiments, the NS1 protein inhibitor may comprise between about 2% to about 75% of the weight of the unit, or between about 25% to about 60%, for example, and any range derivable therein. In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In any case, the composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal, or combinations thereof.

The NS1 protein inhibitor may be formulated into a composition in a free base, neutral, or salt form. Pharmaceutically acceptable salts include acid addition salts, e.g., those formed with the free amino groups of a proteinaceous composition, or which are formed with inorganic acids such as for example, hydrochloric or phosphoric acids, or such organic acids as acetic, oxalic, tartaric, or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine, or procaine. Other bases and salts are described herein.

In embodiments where the composition is in a liquid form, a carrier can be a solvent or dispersion medium comprising but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. It may be preferable to include isotonic agents, such as, for example, sugars, sodium chloride, or combinations thereof.

In other embodiments, one may use eye drops, nasal solutions or sprays, aerosols or inhalants in the present invention. Such compositions are generally designed to be compatible with the target tissue type. In a non-limiting example, nasal solutions are usually aqueous solutions designed to be administered to the nasal passages in drops or sprays. Nasal solutions are prepared so that they are similar in many respects to nasal secretions, so that normal ciliary action is maintained. Thus, in certain embodiments the aqueous nasal solutions usually are isotonic or slightly buffered to maintain a pH of about 5.5 to about 6.5. In addition, antimicrobial preservatives, similar to those used in ophthalmic preparations, drugs, or appropriate drug stabilizers, if required, may be included in the formulation. For example, various commercial nasal preparations are known and include drugs such as antibiotics or antihistamines.

In certain embodiments the candidate substance is prepared for administration by such routes as oral ingestion. In these embodiments, the solid composition may comprise, for example, solutions, suspensions, emulsions, tablets, pills, capsules (e.g., hard or soft shelled gelatin capsules), sustained release formulations, buccal compositions, troches, elixirs, suspensions, syrups, wafers, or combinations thereof. Oral compositions may be incorporated directly with the food of the diet. In certain embodiments, carriers for oral administration comprise inert diluents (e.g., glucose, lactose, or mannitol), assimilable edible carriers or combinations thereof. In other aspects of the invention, the oral composition may be prepared as a syrup or elixir. A syrup or elixir, and may comprise, for example, at least one active agent, a sweetening agent, a preservative, a flavoring agent, a dye, a preservative, or combinations thereof.

In certain embodiments an oral composition may comprise one or more binders, excipients, disintegration agents, lubricants, flavoring agents, or combinations thereof. In certain embodiments, a composition may comprise one or more of the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc.; or combinations thereof the foregoing. When the dosage unit form is a capsule, it may contain, in addition to materials of the above type, carriers such as a liquid carrier. Various other materials may be present as coatings or to otherwise modify the physical form of the dosage unit. For instance, tablets, pills, or capsules may be coated with shellac, sugar, or both.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, certain methods of preparation may include vacuum-drying or freeze-drying techniques which yield a powder of the active ingredient plus any additional desired ingredient from a previously sterile-filtered liquid medium thereof. The liquid medium should be suitably buffered if necessary and the liquid diluent (e.g., water) first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

In particular embodiments, prolonged absorption of an injectable composition can be brought about by the use in the compositions of agents delaying absorption, such as, for example, aluminum monostearate, gelatin, or combinations thereof.

G. Combination Therapy

In order to enhance or increase the effectiveness of an NS1 protein inhibitor of the present invention, the NS1 protein inhibitor may be combined with another therapy, such as another agent that combats viral infection. For example, NS1 protein inhibitors of the present invention may be provided in a combined amount with an effective amount another agent to reduce or block viral replication in infected cells. It is contemplated that this type of combination therapy may be used in vitro or in vivo. In a non-limiting example, an agent that combats viral infections may be an influenza virus neuraminidase inhibitor (e.g., Relenza™ or Tamiflu™). Another non-limiting example of an agent that combats viral infections is an M2 proton channel inhibitor (e.g., amantadine or rimantadine).

These processes may involve administering the agents at the same time or within a period of time wherein separate administration of the substances produces a desired therapeutic benefit. This may be achieved by contacting the cell, tissue, or organism with a single composition or pharmacological formulation that includes two or more agents, or by contacting the cell with two or more distinct compositions or formulations, wherein one composition includes one agent and the other includes another.

The compounds of the present invention may precede, be co-current with and/or follow the other agents by intervals ranging from minutes to weeks. In embodiments where the agents are applied separately to a cell, tissue or organism, one would generally ensure that a significant period of time did not expire between the time of each delivery, such that the agents would still be able to exert an advantageously combined effect on the cell, tissue or organism. For example, in such instances, it is contemplated that one may contact the cell, tissue or organism with two, three, four or more modalities substantially simultaneously (i.e., within less than about a minute) as the candidate substance. In other aspects, one or more agents may be administered about 1 minute, about 5 minutes, about 10 minutes, about 20 minutes about 30 minutes, about 45 minutes, about 60 minutes, about 2 hours, about 3 hours, about 4 hours, about 5 hours, about 6 hours, about 7 hours about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 22 hours, about 23 hours, about 24 hours, about 25 hours, about 26 hours, about 27 hours, about 28 hours, about 29 hours, about 30 hours, about 31 hours, about 32 hours, about 33 hours, about 34 hours, about 35 hours, about 36 hours, about 37 hours, about 38 hours, about 39 hours, about 40 hours, about 41 hours, about 42 hours, about 43 hours, about 44 hours, about 45 hours, about 46 hours, about 47 hours, about 48 hours, about 1 day, about 2 days, about 3 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20 days, about 21 days, about 1, about 2, about 3, about 4, about 5, about 6, about 7 or about 8 weeks or more, and any range derivable therein, prior to and/or after administering the candidate substance.

Various combination regimens of the agents may be employed. Non-limiting examples of such combinations are shown below, wherein an NS1 protein inhibitor is "A" and a second agent, such as a neuraminidase inhibitor, is "B":

| | | | | | | | |
|---|---|---|---|---|---|---|---|
| A/B/A | B/A/B | B/B/A | A/A/B | A/B/B | B/A/A | A/B/B/B | B/A/B/B |
| B/B/B/A | B/B/A/B | A/A/B/B | A/B/A/B | A/B/B/A | B/B/A/A | | |
| B/A/B/A | B/A/A/B | A/A/A/B | B/A/A/A | A/B/A/A | A/A/B/A | | |

H. EXAMPLES

The following examples are included to demonstrate certain preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

NS1 Protein Binds Host mRNA Export Factors Blocking Expression of Antiviral Genes NS1 protein forms an inhibitory complex with the mRNA export factors NXF1-p15, Rae1, and E1B-AP5 (Satterly et al., 2007), which are key constituents of the mRNA export machinery that interact with both mRNAs and nucleoporins, such as Nup98, to direct mRNAs through the nuclear pore complex (NPC) (Stutz and Izaurralde, 2003) (FIG. 1B). The mRNA export receptors NXF1-p15 (TAP-NXT) are responsible for nuclear exit of ~70% of cellular mRNAs (Stutz and Izaurralde, 2003). This heterodimer interacts with both messenger ribonucleoprotein particles (mRNPs) and nuclear pore complex proteins (nucleoporins or Nups) to translocate mRNAs through the NPC (Stutz and Izaurralde, 2003). E1B-AP5, identified as a cellular protein that interacts with the adenovirus protein E1B-55 (Geiss et al., 2002), is an hnRNP-like protein that likely mediates the interaction of NXF1 with mRNAs (Bachi et al., 2000). Furthermore, the mRNA export factor Rae1/mrnp41/Gle2 (Brown et al., 1995; Kraemer and Blobel, 1997; Murphy et al., 1996), which shuttles between the nucleus and the cytoplasm, forms a complex with RNPs (Kraemer and Blobel, 1997; Pritchard et al., 1999), NXF1 (Blevins et al., 2003), and the nucleoporin Nup98 (Pritchard et al., 1999). It has been proposed that Rae1 may recruit NXF1 to Nup98 to mediate transport of mRNPs through the NPC (Blevins et al., 2003). The VSV matrix (M) protein, which inhibits bulk mRNA nuclear export (Enninga et al., 2002; Her et al., 1997; von Kobbe et al., 2000), interacts with Rae1 that is in complex with Nup98 (Faria et al., 2005).

However, this mRNA export block can be fully reverted by increasing the intracellular levels of Rae1 (Faria et al., 2005) or partially reverted by inducing higher levels of Nup98-Nup96 (Enninga et al., 2002). Significantly, Nup98-Nup96 and Rae1 are IFN-stimulated gene products (Enninga et al., 2002; Faria et al., 2005) and treatment of cells with IFN reverts the mRNA export blockade mediated by VSV M protein (Enninga et al., 2002). These findings support an important role for the mRNA export machinery in both viral pathogenesis and host antiviral responses.

Analogous to previous findings by the present inventors concerning VSV M protein (Enninga et al., 2002; Faria et al., 2005), the inventors have found that the mRNA export block induced by NS1 protein is reverted by increased levels of NXF1, p15, or Rae1 (Satterly et al., 2007).

Example 2

Influenza Virus Inhibits Host Poly(A) RNA Nuclear Export—Part I

The NS1 protein of influenza virus has been shown to inhibit nuclear export of host mRNAs when expressed in mammalian cells (Qiu and Krug, 1994). To examine the importance of regulated bulk mRNA export in the context of viral infection, the distribution of host poly(A) RNA in influenza virus infected MDCK cells was determined, and nuclear export was found to be impaired (FIG. 2A). Expression of influenza proteins in MDCK cells was clearly detected by immunoblot analysis, starting at 4 hours post-infection (FIG. 2B). Inhibition of mRNA export was observed as early as 6 h post-infection (FIG. 2A), a time that allowed easy detection of infected cells using polyclonal antibodies against influenza proteins. However, this inhibitory effect on mRNA export may begin even earlier, as a key constituent of the mRNA export machinery is degraded at early stages of infection (see below). The inhibition of mRNA export was enhanced by 12 h of infection and was selective for host mRNA, since viral proteins were expressed throughout the course of infection.

Example 3

Influenza Virus Inhibits Host Poly(A) RNA Nuclear Export—Part II

Whether NS1 protein interacted with the mRNA nuclear export machinery was investigated. Purified GST-NS1 protein or GST alone was incubated with cell extracts from 293T cells. As shown in FIG. 3A, NS1 protein interacted with NXF1, p15, E1B-AP5 and Rae1. In contrast, no interaction of NS1 protein was detected with other constituents of the nuclear transport machinery including Nup96, Nup62, Nup153, and Nup214 (FIGS. 3B and 3C). These results indicate that NS1 protein binds specifically to the mRNA factors NXF1, p15, E1B-AP5, and Rae1, which are known to form a complex (Bachi et al., 2000; Blevins et al., 2003).

The first 73 amino acids of NS1 protein bind dsRNA with low affinity (Krug et al., 2003) and amino acids 19 to 38 are required for NS1 protein-mediated inhibition of mRNA nuclear export as are amino acids 134 to 161 at the carboxyl terminus (Qian et al., 1994). Deletion of the first 48 or 72 amino acids of NS1 protein inhibited its interaction with NXF1 and Rae1, and decreased considerably its interaction with E1B-AP5 (FIG. 3D). However, proteins lacking the first 48 or 73 residues of NS1 protein retained significant interaction with endogenous p15 (FIG. 3D). On the other hand, NXF1, Rae1 and E1B-AP5 bound poorly to the amino terminal domain of NS1 protein (amino acids 1-73), and p15 showed no significant interaction with this domain. These results demonstrate that p15 interacts with the carboxyl terminal domain of NS1 protein whereas NXF1, Rae1 and E1B-AP5 binding requires residues within the amino and carboxyl terminal domains of NS1 protein. Interaction of NS1 protein with NXF1, p15 and Rae1 is not dependent on RNA, as incubation of cell extracts with RNase A did not affect these interactions (FIG. 3E). However, interaction of E1B-AP5 with NS1 protein was diminished in the present of RNase A indicating partial dependence on RNA.

These findings demonstrate that NS1 protein is able to interact with constituents of the mRNA nuclear export machinery and that NS1 protein may cause a rearrangement of the NXF1/p15/E1B-AP5/Rae1-complex, resulting in inhibition of mRNA nuclear export. Alternatively, NS1 protein may mask binding sites of this mRNA export complex preventing its proper interaction with other constituents of the mRNA export pathway. To investigate additional effects of influenza virus on the mRNA nuclear export machinery, the levels of constituents of this machinery following infection of 293T and MDCK cells were determined. Nup98 levels were found to be markedly depleted at approximately 2-4 h after infection of 293T cells and by 24 h in MDCK cells (FIGS. 3F and 3G). No major differences in the levels of Rae1, NXF1, E1B-AP5, Nup153, and Nup62 were detected. Whether the observed changes in Nup98 levels are a consequence of general inhibition of protein synthesis by influenza virus was then tested. FIG. 3H shows that Nup98 has a long half-life, which indicates that it is actively degraded during influenza virus infection. This degradation likely contributes to the inhibition of mRNA nuclear export observed upon influenza infection.

Example 4

Increased Expression of mRNA Export Factors Maintains Nuclear Export of mRNA in the Presence of NS1 Protein To determine if blocking mRNA nuclear export is critical for influenza virus mediated-inhibition of host gene expression, the inventors tested whether increasing expression of mRNA export factors could prevent this inhibition. As shown in FIG. 4A, increased levels of NXF1, p15, Rae1, or Nup98, but not of Nup96, decreased the inhibition of gene expression mediated by NS1 protein in a dose-dependent manner. Nup96 is a nucleoporin that does not form a complex with NXF1/p15 but has a role in mRNA export (Boehmer et al. 2003; Faria et al., 2006; Vasu et al., 2001). These results show that the reversal of NS1 protein function is specific for constituents of the NXF1/p15 complex, which includes Nup98 and Rae1. To demonstrate that both the inhibition of host gene expression by NS1 protein and its reversal occurred at the mRNA export level, immunofluorescence and oligo-dT in situ hybridization was performed in cells expressing NS1 protein alone or co-expressing NXF1/p15. As shown in FIG. 4B, expression of NS1 protein caused nuclear retention of poly(A) RNA, and this effect was significantly blocked in cells that co-expressed NS1 protein and NXF1/p15. Thus, these results show that mRNA export factors can antagonize the action of NS1 protein on mRNA nuclear export.

Example 5

Influenza Virus Virulence Correlates with Impaired Nuclear Export Function

Figure 6:
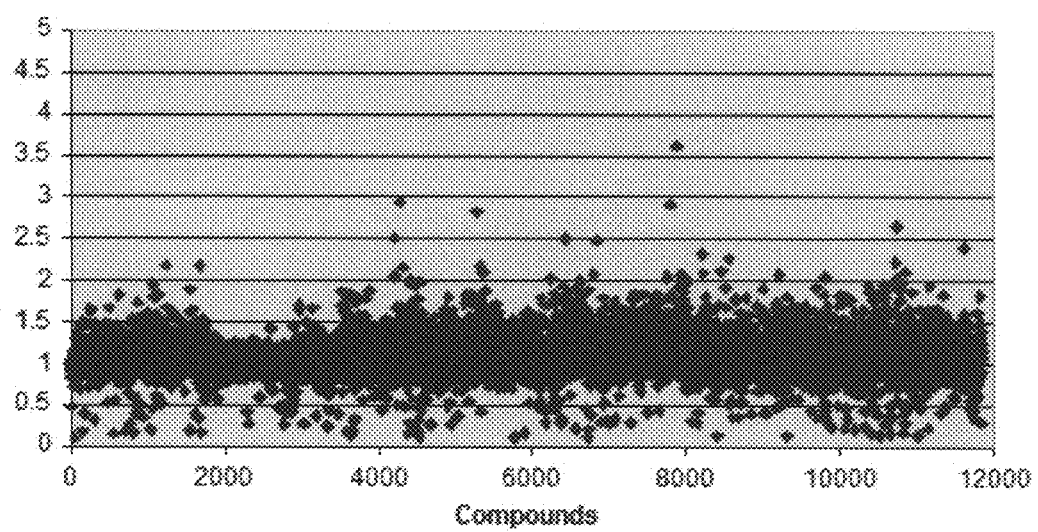
FIG. 6. Data from one day's screen (12,000 compounds). In all, 200,000 compounds were screened for the ability to antagonize the inhibition of luciferase expression by NS1 protein. The average plate Z' score for the experiment was 0.64.
Figure 8:
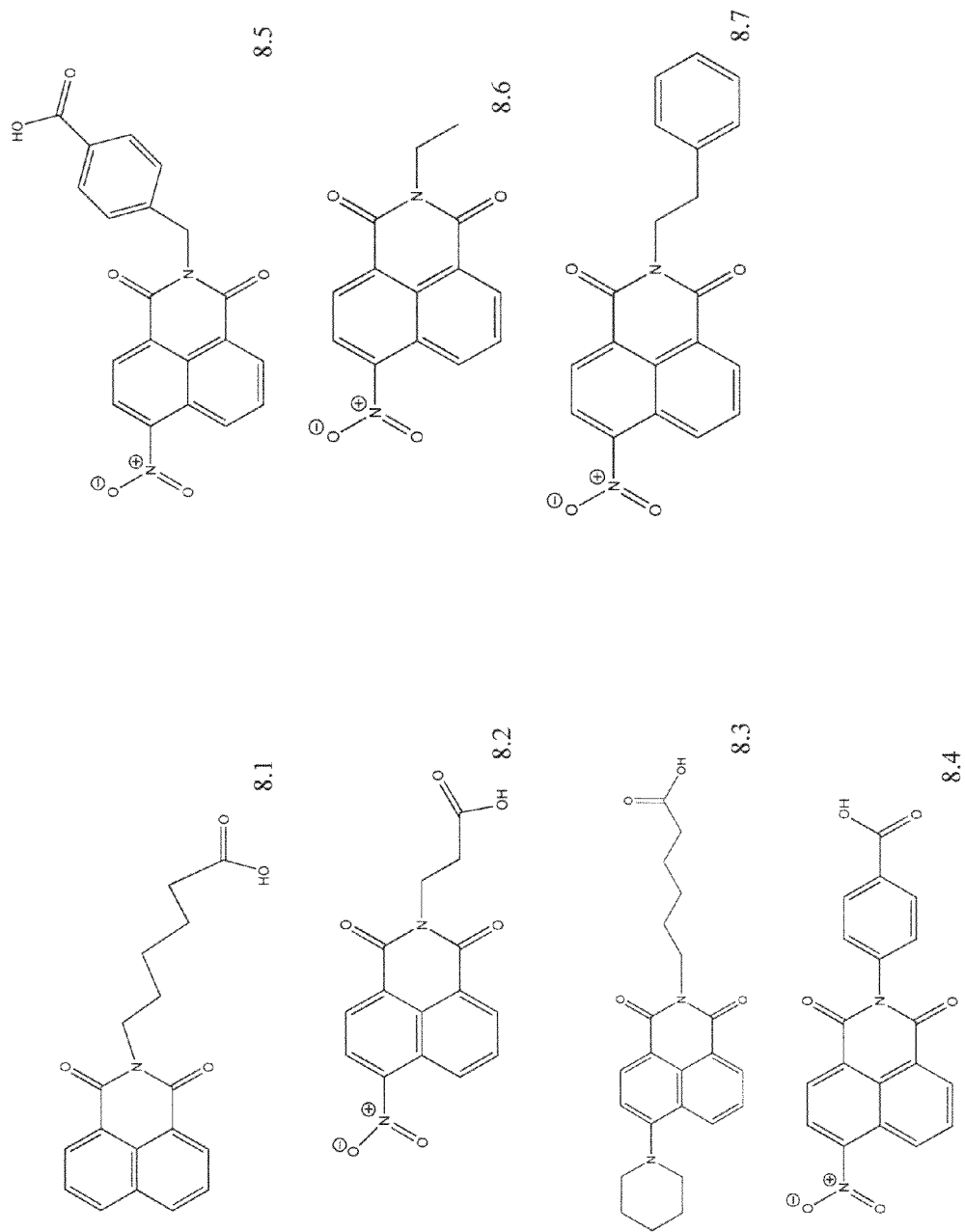
FIGS. 8-9. Additional compounds of the present invention.
Figure 9:
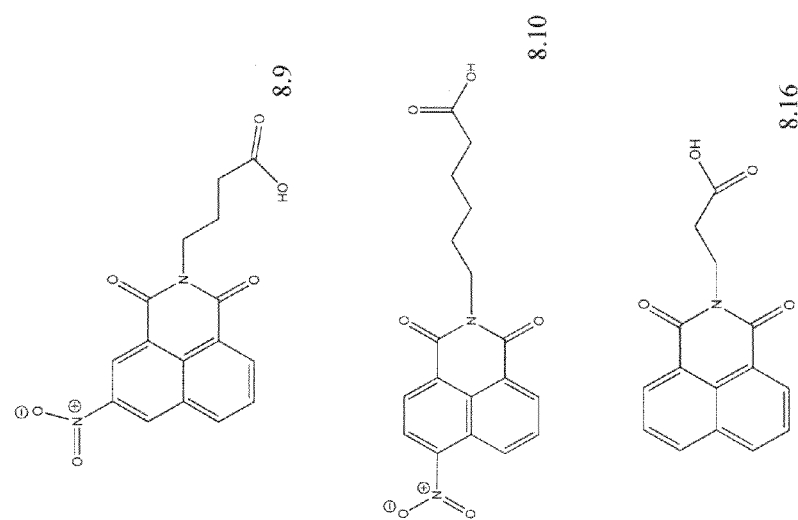

Through analyzing their data, the inventors predicted that cells from mice that express low levels of key constituents of the mRNA nuclear export machinery should have increased susceptibility to influenza infection. Therefore, Rae1+/− or Nup98+/− cells from mice, which respectively express low levels of Rae1 or Nup98, and normal levels of other nuclear export factors were each tested (Faria et al., 2005; Jeganathan et al., 2005). Rae1+/− Nup98+/− double heterozygotes, which express low levels of both Rae1 and Nup98, were also tested (Jeganathan et al., 2005). Rae1+/− or Nup98+/− cells were more susceptible to influenza virus-mediated cell death than wild-type cells, and cells that were double heterozygous for Rae1 and Nup98 demonstrated an enhanced susceptibility (FIGS. 5A and 5B). These cells also produced more virus compared to the wild-type cells (FIG. 5C). Thus, the mRNA export machinery plays a key role in antiviral responses. Interestingly, the inventors observed more virus in the supernatants of Rae1+/− cells as compared to Nup98+/− or Rae1+/− Nup98+/− cells, despite the fact that the later cell types showed more cell death than the Rae1+/− cells (FIGS. 6A and 6B). This may indicate that viral replication as observed in Rae1+/− cells requires wild-type levels of Nup98, or that the enhanced cytopathology due to more impaired mRNA export prevented efficient viral replication.

Example 6

Small Molecule Library Screen for NS1 Protein Inhibitors

An assay was developed for high-throughput screening of 200,000 small molecules available from a library owned by the University of Texas, Southwestern, at several concentrations, as well as a secondary assay for testing the ability of chemicals to block cell death caused by multicycle influenza virus replication (i.e., inhibit influenza A virus cytopathic effect) in epithelial cells. For the primary screen, 293T cells were transfected with plasmids encoding NS1 protein and luciferase, or with the luciferase plasmid alone as control, and 16 hours later the cells were transferred to the wells of 384-well microtiter plates. Compounds dissolved in dimethylsulfoxide (DMSO) were added to the wells at a final concentration of 5 μM compound in 1% DMSO. On each plate, some wells received the same final concentration of the DMSO solvent alone as controls. The cells were incubated for 22 hours and the luciferase substrate luciferin was added to the wells in the appropriate buffer; the amount of light generated by luciferase was detected with a Perkin Elmer Envision plate reader operating in luminescence mode. Wells emitting significantly more light than wells treated with the DMSO solvent alone were identified as containing compounds potentially of interest. The experiment was repeated with these compounds of interest at concentrations of 15 μM, 5 μM and 1.67 μM and the most active compounds were identified.

In a secondary screen, MDCK epithelial cells in 384-well microtiter plates were infected with A/WS/33 influenza A virus at a low multicity of infection that would necessitate multiple round of virus growth to kill all of the cells. Compounds identified as of interest in the primary screen were added to the wells of these plates. On each plate, some wells received the DMSO solvent alone as control and some wells were not infected as a second control group. After 52 hours cell viability was measured with CelTiterGlo reagent from Promega. Wells in which cell viability was 20% of the uninfected controls, or higher, were identified as containing compounds of interest.

As expected, the best NS1 protein inhibitors also inhibited virus cytopathic effects. It is important to note, that with the exception of one compound (8 in FIG. 7), the values shown are from the screening experiments using compounds for which only estimated concentrations and solubilities were available. Inhibitor 8 has been purchased in large quantities from Chemical Diversity Laboratories (San Diego, Calif.) and its purity and concentration verified prior to obtaining the data on inhibition of virus killing in human bronchial epithelial cells. Although 8 was not one of the most active compounds in the original screen, it was most potent in the infection assay. It is possible that some of the other compounds will show improvements in potency once pure stocks of known concentration are obtained (see FIG. 7). In a secondary screen of the best 640 NS1 protein inhibitors, 71 were selected that also inhibited influenza virus-mediated cell death. From these 71 inhibitors, 8 different compound families were chosen for further analyses (see FIG. 7).

Additional NS1 protein inhibitory compounds were later identified (see FIGS. 8-9). These may be purchased from Chemical Diversity Laboratories (San Diego, Calif.) or ChemBridge Corp. (San Diego, Calif.). Compounds 8.3 and 8.6 were found to be more inhibitory of NS1 protein and also more inhibitory of virus growth than compound 8, which was previously identified. Compound 8.3 was among analogs of compound 8 that were purchased and tested for their ability to inhibit influenza virus growth and, in parallel, in the assay described above that relies upon a luciferase reporter. Compound 8.3 was the most potent compound for inhibiting virus growth, but did not score in the luciferase dependent assay. Compound 8.3 was then tested for its ability to inhibit luciferase expression in the absence of NS1 protein and it was found to be an inhibitor of firefly luciferase expression. We also tested compound 8.3 for the ability to inhibit expression of *Renilla* luciferase expression, and the compound had no effect. Therefore, 8.3 inhibits firefly luciferase specifically. It is known in the art that various compounds inhibit firefly luciferase, and approximately 300 compounds in the compound library described above inhibit this common reporter.

Example 7

Toxicity Studies

| Compound | MDCK toxicity 24 hr | MDCK toxicity 36 hr | WSN HA titer 24H 24 hr | WSN HA titer 24H 36 hr |
|---|---|---|---|---|
| 8.0 | 1.03 | 0.90 | 0.50 | 0.50 |
| 8.1 | 1.03 | 0.97 | 1.00 | 0.50 |
| 8.2 | 0.98 | 0.89 | 0.25 | 0.50 |
| 8.3 | 0.88 | 0.90 | 0.13 | 0.13 |
| 8.4 | 1.02 | 0.88 | ND | ND |
| 8.5 | 0.62 | 0.65 | ND | ND |
| 8.6 | 0.36 | 0.31 | 0.13 | 0.25 |
| 8.7 | 0.18 | 0.29 | ND | ND |
| 8.9 | 0.98 | 0.81 | 0.50 | 0.50 |
| 8.10 | 0.46 | 0.68 | 0.13 | 0.19 |
| 8.16 | 0.96 | 0.90 | 1.00 | 0.50 |

ND: not determined.

See FIGS. 7-9 for structures of compounds.

For measuring toxicity on MDCK cells, compounds were added to MDCK cells at a final concentration of 20 μM compound in 1% DMSO in microtiter plates and at 24 and 36 hours the ATP present in the wells was measured with CelTiterGlo reagent. Values were normalized to samples treated with the DMSO diluent alone. A value of 1.0 means compounds are completely nontoxic.

In the HA test, cultures were infected with influenza virus under conditions that require multiple cycles of infection to kill all cells in the culture and treated with 20 μM compound or with DMSO alone. The culture medium was then serially diluted and tested for the ability of influenza virus to bind to, aggregate and precipitate chicken erythrocytes (hemagglutination). This is a simple method for measuring virus particles in cell culture medium. Values for compounds are normalized to the value of the DMSO control. A value of 1.0 means no inhibition of virus growth.

************************

All of the methods and apparatuses disclosed and claimed herein can be made and executed without undue experimentation in light of the present disclosure. While the compositions and methods of this invention have been described in terms of preferred embodiments, it will be apparent to those of skill in the art that variations may be applied to the methods and apparatuses and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Akira et al., *Cell,* 124:783-801, 2006.
Bachi et al., *RNA,* 6:136-158, 2000.
Blevins et al.I, *J. Biol. Chem.,* 278:20979-20988, 2003.
Boehmer et al., *Proc. Natl. Acad. Sci. USA,* 100:981-985, 2003.
Brown et al., *J. Biol. Chem.,* 270:7411-7419, 1995.
Bundgaard, *Drugs of the Future,* 16:443-458, 1991.
Bundgaard, In: *Design of Prodrugs,* 7-9, 21-24, Elsevier, Amsterdam, 1985.
Chen et al., *Embo. J,* 18:2273-2283, 1999.
Donelan et al., *J. Virol.,* 77:13257-13266, 2003.
Donelan et al., *J. Virol.,* 78:11574-11582, 2004.
Douglas, *New Engl. J. of Med.,* 322:443-450, 1990.
Enninga et al., *Science,* 295:1523-1525, 2002.
Faria et al., *Immunity,* 24:295-304, 2006.
Faria et al., *Molec. Cell,* 17:93-102, 2005.
Garcia-Sastre et al., *Virology,* 252:324-330, 1998.
Garcia-Sastre et al., *Virology,* 252:324-330, 1998.
Geiss et al., *Proc. Natl. Acad. Sci. USA,* 99:10736-10741, 2002.
Greene and Wuts, In: *Protecting Groups in Organic Synthesis,* 3rd Ed., John Wiley & Sons, Inc., 1999.
Guillot et al., *J. Biol. Chem.,* 280:5571-5580, 2005.
Guo et al., *Am. J. Respir. Cell Mol. Biol.,* 36(3):263-269, 2006.
*Handbook of Pharmaceutical Salts: Properties, Selection and Use*, Stahl and Wermuth (Eds.), Verlag Helvetica Chimica Acta, 2002.
Her et al., *Science,* 276:1845-1848, 1997.
Jeganathan et al., *Nature,* 438:1036-1039, 2005.
Kawai and Akira, *Nature immunol,* 7:131-137, 2006.
Knipe and Howley, In: *Fields Virology,* 4th Ed., 1:1487-1531, 2001.
Kraemer and Blobel, *Proc. Natl. Acad. Sci. USA,* 94:9119-9124, 1997.
Krug et al., *Virology,* 309:181-189, 2003.
Le Goffic et al., *J. Immunol.,* 178:3368-3372, 2007.
Le Goffic et al., *PLoS pathogens,* 2:e53, 2006.
Levy and Garcia-Sastre, *Cytokine Growth Factor Rev.,* 12:143-156, 2001.
Li et al., *Virology,* 349:13-21, 2006.
Marie et al., *Embo. J,* 17:6660-6669, 1998.
Mibayashi et al., *J. Virol.,* [Epub ahead of print], 2006.
Min and Krug, *Proc. Natl. Acad. Sci. USA,* 103:7100-7105, 2006.
Murphy et al., *Molec. Biol. Cell,* 7:1921-1937, 1996.
Nemeroff et al., *Mol. Cell,* 1:991-1000, 1998.
Noah et al., *Virology,* 307:386-395, 2003.
Opitz et al., *Cell Microbiol*. [Epub ahead of print], 2006.
Pichlmair et al., *Science,* 314:997-1001, 2006.
Pritchard et al., *J. Cell Biol.,* 145:237-254, 1999.
Qian et al., *J. Virol.,* 68:2433-2441, 1994.
Qiu and Krug, *J. Virol.,* 68:2425-2432, 1994.
Remington's Pharmaceutical Sciences, pp 1289-1329, 1990
Rochette-Egly, *J. Biol. Chem.,* 280:32565-32568, 2005.
Satterly et al., *Proc. Natl. Acad. Sci. USA,* 104:1853-1858, 2007.
Sen and Lengyel, *J. Biol. Chem.,* 267:5017-5020, 1992.
Smith et al., *Science* 305:371-376, 2004.
Smith and March, In: *Advanced Organic Chemistry: Reactions, Mechanisms, and Structure,* 5th Ed., John Wiley & Sons, Inc., New York, 2001.
Stut and Izaurralde, *Trends Cell Biol.,* 13:319-327, 2003.
Talon et al., *J. Virol.,* 74:7989-7996, 2000.
Taniguchi and Takaoka, *Nature Rev.,* 2:378-386, 2001.
Twu et al., *J. Virol.,* 80:3957-3965, 2006.
Vasu et al., *J. Cell Biol.,* 155: 339-354, 2001.
von Kobbe et al., *Molecul., Cell,* 6:1243-1252, 2000.
Webster, *Proc. Natl. Acad. Sci. USA,* 96:1164-1166, 1999.

What is claimed is:

1. A method of attenuating a viral infection in a patient, wherein said viral infection is selected from the group consisting influenza A virus, influenza B virus, a bunyavirus, an arenavirus, an encephalitis virus, rabies and a filovirus, comprising administering to said patient an amount of a non-structural 1 (NS1) protein inhibitor effective to attenuate said viral infection, wherein the NS1 protein inhibitor compound is a compound of formula (XIII)

(XIII)

wherein $R_x$ and $R_y$ are each independently lower alkyl, or $R_x$ and $R_y$ are joined to form a piperidinyl, pyrrolidinyl, or pyridinyl ring; and $_f$ is 1-5.

2. The method of claim 1, wherein $R_x$ and $R_y$ are joined to form a piperidinyl ring.

3. The method of claim 1, wherein the viral infection is influenza.

4. The method of claim 1, wherein the method of administration is selected from the group consisting of an inhaled aerosol, nasal spray, oral formulation and injection.

5. The method of claim 1, wherein the dose of NS1 protein inhibitor that is administered is about 1 mg/kg to about 50 mg/kg.

6. A method of reducing the duration of a viral infection in a patient, wherein said viral infection is selected from the group consisting influenza A virus, influenza B virus, a bunyavirus, an arenavirus, an encephalitis virus, rabies and a filovirus, comprising administering to said patient an amount of an NS1 protein inhibitor effective to reduce the duration of said viral infection, wherein the NS1 protein inhibitor compound is a compound of formula (XIII)

(XIII)

wherein $R_x$ and $R_y$ are each independently lower alkyl, or $R_x$ and $R_y$ are joined to form a piperidinyl, pyrrolidinyl, or pyridinyl ring; and $f$ is 1-5.

7. The method of claim 6, wherein the viral infection is influenza.

8. The method of claim 6, wherein the viral infection is caused by the influenza A virus.

9. A method of attenuating a viral infection in a patient, wherein said viral infection is selected from the group consisting influenza A virus, influenza B virus, a bunyavirus, an arenavirus, an encephalitis virus, rabies and a filovirus, comprising administering to said patient an amount of a non-structural 1 (NS1) protein inhibitor in combination with a neuraminidase inhibitor selected from the group consisting of zanamivir and oseltamivir, effective to attenuate said viral infection, wherein the NS1 protein inhibitor compound is a compound of formula (XIII)

(XIII)

wherein $R_x$ and $R_y$ are each independently lower alkyl, or $R_x$ and $R_y$ are joined to form a piperidinyl, pyrrolidinyl, or pyridinyl ring; and $f$ is 1-5.

* * * * *

UNITED STATES PATENT AND TRADEMARK OFFICE
CERTIFICATE OF CORRECTION

PATENT NO.      : 8,119,656 B2
APPLICATION NO. : 12/315945
DATED           : February 21, 2012
INVENTOR(S)     : Michael Roth et al.

It is certified that error appears in the above-identified patent and that said Letters Patent is hereby corrected as shown below:

In claim 6, column 51, lines 25-35, delete chemical drawing and insert

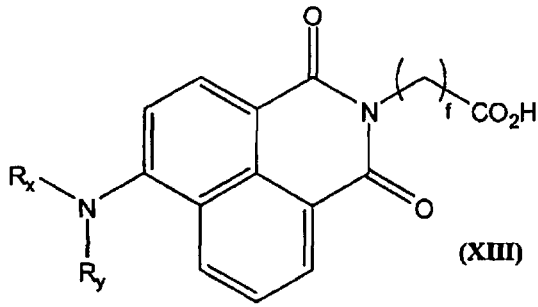

-- -- therefor.

In claim 9, column 52, lines 20-30, delete chemical drawing and insert

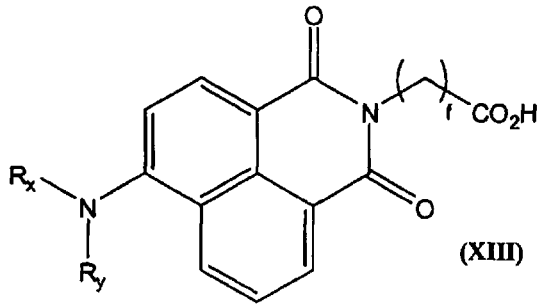

-- -- therefor.

Signed and Sealed this
Tenth Day of April, 2012

David J. Kappos
*Director of the United States Patent and Trademark Office*